(12) United States Patent
Shelton, IV et al.

(10) Patent No.: US 10,433,925 B2
(45) Date of Patent: Oct. 8, 2019

(54) STERILE BARRIER FOR ROBOTIC SURGICAL SYSTEM

(71) Applicant: Ethicon Endo-Surgery, LLC, Guaynabo, PR (US)

(72) Inventors: Frederick E. Shelton, IV, Hillsboro, OH (US); Jason L. Harris, Lebanon, OH (US); Jeffrey S. Swayze, Hamilton, OH (US); Michael J. Vendely, Lebanon, OH (US)

(73) Assignee: Ethicon LLC, Guanyabo, PR (US)

( * ) Notice: Subject to any disclaimer, the term of this patent is extended or adjusted under 35 U.S.C. 154(b) by 368 days.

(21) Appl. No.: 15/237,721

(22) Filed: Aug. 16, 2016

(65) Prior Publication Data

US 2018/0049833 A1 Feb. 22, 2018

(51) Int. Cl.
*A62B 19/00* (2006.01)
*A61B 46/10* (2016.01)
*A61B 34/30* (2016.01)
*A61B 17/00* (2006.01)

(52) U.S. Cl.
CPC .............. *A61B 46/10* (2016.02); *A61B 34/30* (2016.02); *A61B 2017/00477* (2013.01)

(58) Field of Classification Search
CPC ......... A61B 34/30; A61B 34/32; A61B 34/35; A61B 34/37; A61B 46/10; A61B 46/23; A61B 1/00142
See application file for complete search history.

(56) References Cited

U.S. PATENT DOCUMENTS

| | | | |
|---|---|---|---|
| 8,114,345 B2 | 2/2012 | Dlugos, Jr. et al. | |
| 8,206,406 B2 * | 6/2012 | Orban, III | A61B 34/30 |
| | | | 606/130 |
| 8,882,792 B2 | 11/2014 | Dietz et al. | |
| 8,915,842 B2 | 12/2014 | Weisenburgh, II et al. | |
| 8,931,682 B2 | 1/2015 | Timm et al. | |
| 8,945,098 B2 | 2/2015 | Seibold et al. | |
| 2008/0081948 A1 | 4/2008 | Weisenburgh et al. | |
| 2011/0118709 A1 | 5/2011 | Burbank | |

(Continued)

OTHER PUBLICATIONS

Correlated Solutions, "Principle of Digital Image Correlation," 2013 (http://correlatedsolutions.com/digital-image-correlation/).

(Continued)

*Primary Examiner* — Kari K Rodriquez
*Assistant Examiner* — Camtu T Nguyen
(74) *Attorney, Agent, or Firm* — Mintz Levin Cohn Ferris Glovsky and Popeo, P.C.

(57) ABSTRACT

A sterile barrier is provided for use with a surgical robotic system. The sterile barrier can include a housing configured to mate with a tool driver mated to a robotic arm and to removably receive a surgical tool. The housing of the sterile barrier has a sterile flexible fabric extending therefrom such that the housing and the flexible fabric are formed in more than one plane and define a sterile side on which the surgical tool is disposed and a non-sterile side on which the tool driver and the robotic arm are disposed. The housing has an opening for receiving the surgical tool. The housing can have at least one electrical contact configured to operably mate with at least one complementary electrical contact on at least one of the tool driver and the robotic arm.

13 Claims, 16 Drawing Sheets

(56) References Cited

U.S. PATENT DOCUMENTS

2011/0118778 A1 5/2011 Burbank
2013/0282052 A1 10/2013 Aranyi et al.
2014/0005718 A1 1/2014 Shelton, IV et al.

OTHER PUBLICATIONS

U.S. Appl. No. 15/131,963 entitled "Method for Operating a Surgical Instrument" filed Apr. 18, 2016.
U.S. Appl. No. 15/177,430 entitled "Surgical Instrument With User Adaptable Techniques" filed Jun. 9, 2016.

* cited by examiner

STERILE BARRIER FOR ROBOTIC SURGICAL SYSTEM

FIELD OF THE INVENTION

Methods and devices are provided for robotic surgery, and in particular for providing effective sterile barriers for use with a robotic surgical system.

BACKGROUND OF THE INVENTION

Minimally invasive surgical (MIS) instruments are often preferred over traditional open surgical devices due to the reduced post-operative recovery time and minimal scarring. Laparoscopic surgery is one type of MIS procedure in which one or more small incisions are formed in the abdomen and a trocar is inserted through the incision to form a pathway that provides access to the abdominal cavity. The trocar is used to introduce various instruments and tools into the abdominal cavity, as well as to provide insufflation to elevate the abdominal wall above the organs. The instruments and tools can be used to engage and/or treat tissue in a number of ways to achieve a diagnostic or therapeutic effect. Endoscopic surgery is another type of MIS procedure in which elongate flexible shafts are introduced into the body through a natural orifice.

Although traditional minimally invasive surgical instruments and techniques have proven highly effective, newer systems may provide even further advantages. For example, traditional minimally invasive surgical instruments often deny the surgeon the flexibility of tool placement found in open surgery. Difficulty is experienced in approaching the surgical site with the instruments through the small incisions. Additionally, the added length of typical endoscopic instruments often reduces the surgeon's ability to feel forces exerted by tissues and organs on the end effector. Furthermore, coordination of the movement of the end effector of the instrument as viewed in the image on the television monitor with actual end effector movement is particularly difficult, since the movement as perceived in the image normally does not correspond intuitively with the actual end effector movement. Accordingly, lack of intuitive response to surgical instrument movement input is often experienced. Such a lack of intuitiveness, dexterity and sensitivity of endoscopic tools has been found to be an impediment in the increased the use of minimally invasive surgery.

Over the years a variety of minimally invasive robotic systems have been developed to increase surgical dexterity as well as to permit a surgeon to operate on a patient in an intuitive manner. Telesurgery is a general term for surgical operations using systems where the surgeon uses some form of remote control, e.g., a servomechanism, or the like, to manipulate surgical instrument movements, rather than directly holding and moving the tools by hand. In such a telesurgery system, the surgeon is typically provided with an image of the surgical site on a visual display at a location remote from the patient. The surgeon can typically perform the surgical procedure at the location remote from the patient whilst viewing the end effector movement on the visual display during the surgical procedure. While viewing typically a three-dimensional image of the surgical site on the visual display, the surgeon performs the surgical procedures on the patient by manipulating master control devices at the remote location, which master control devices control motion of the remotely controlled instruments.

While significant advances have been made in the field of robotic surgery, there remains a need for improved methods, systems, and devices for use in robotic surgery.

SUMMARY OF THE INVENTION

Various methods and devices are provided that include a sterile barrier interface for ensuring a sterile surgical environment when performing a telesurgical procedure using a minimally invasive robotic system. The methods and devices are particularly useful in establishing a sterile barrier between the sterile operating area and the non-sterile components of the minimally invasive robotic system. As such, the methods and device are effective in ensuring a sterile interface when performing the surgical operation using the robotic systems.

In one aspect, a sterile barrier for use with a robotic surgical system is provided that in some embodiments includes a housing configured to mate with a tool driver mated to a robotic arm and removably receive a surgical tool. The housing has a sterile flexible fabric extending therefrom such that the housing and the flexible fabric are formed in more than one plane and define a sterile side on which the surgical tool is disposed and a non-sterile side on which the tool driver and the robotic are disposed. The housing has an opening for receiving the surgical tool and at least one electrical contact configured to operably mate with at least one electrical contact on at least one of the tool driver and the robotic arm.

The sterile barrier housing can have a variety of configurations. In some embodiments, the housing includes a substantially rigid and generally cylindrical elongate member having a first side configured to be received within and mated with an opening in the tool driver and a second side opposite of the first side having a housing opening configured to receive the surgical tool. The housing opening is an elongate slit and the housing has a substantially c-shaped cross section. The housing is formed of an annular rim, a first section, and a second section. The annular rim is configured to attach the sterile flexible fabric therefrom such that an exterior portion of the housing defines the sterile side and an interior portion of the housing defines the non-sterile side. The first section has at least one electrical contact to operably mate with at least one electrical contact on at least one of the tool driver and the robotic arm. The second section has a nominal diameter less than the first section to receive an interchangeable shaft coupled to the surgical tool.

In some embodiments, the sterile flexible fabric is formed a polymeric of an elastic membrane. In some embodiment, the sterile barrier includes a coupling ring having an inner surface configured to mate with the tool driver and an outer surface configured to mate with a portion of the surgical tool. The at least one electrical contact of the housing can include a plurality of metal-doped contacts configured to mate on a first side with a plurality of complementary electrical contacts on a portion of the surgical tool and on a second side with a plurality of complementary electrical contacts on a portion of one of the tool driver and the robotic arr. In some embodiments, the complementary electrical contacts on a portion of the surgical tool are formed on a puck portion of the surgical tool.

In another aspects, a surgical method is provided that in some embodiments includes attaching a sterile barrier assembly to a tool driver of a robotic surgical system such that the sterile barrier assembly is operably connected to and in electrical communication with a robotic arm, the sterile barrier assembly defining a non-sterile side and a sterile side with the tool driver being disposed on the non-sterile side. The method also includes mounting a surgical tool within the sterile barrier assembly such that the surgical tool is on the sterile side, the surgical tool being operable connected to and in electrical communication with the sterile barrier assembly and the robotic arm. The method further includes removing the surgical tool from the sterile barrier assembly and remounting the surgical tool or mounting the surgical tool or mounting a second surgical tool within the sterile barrier assembly while the sterile barrier remains attached to the tool driver such that the surgical tool or the second surgical tool is operable connected to and in electrical communication with the sterile barrier assembly and the robotic arm.

The surgical method can vary in different ways. For example, the sterile barrier assembly can include a substantially rigid housing and a flexible fabric. The surgical tool can include at least one electrical contact configured to operably mate with the tool driver and the robotic arm. In some embodiments, the sterile barrier can provide a sterile electrical interface that includes at least one window seal component configured to sealingly receive therethrough at least one electrical contact formed on the tool driver such that the at least one electrical contact formed on the tool driver is operably mated with at least one electrical contact formed on the robotic arm.

In yet other aspects, a surgical method is provided that in some embodiments includes mounting a surgical tool within a sterile barrier assembly such that a surgical tool is on a sterile side, the surgical tool being operably connected with the sterile barrier assembly and a robotic arm. The method also includes penetrating the sterile barrier assembly with the surgical tool configured to move distally and proximally within at least a portion of a sterile environment, and removing the surgical tool from the sterile environment and remounting the surgical tool or mounting a second surgical tool within the sterile barrier assembly and maintaining the sterile environment.

BRIEF DESCRIPTION OF THE DRAWINGS

The present disclosure will be more fully understood from the following detailed description taken in conjunction with the accompanying drawings, in which.

DETAILED DESCRIPTION OF THE INVENTION

Figure 1:
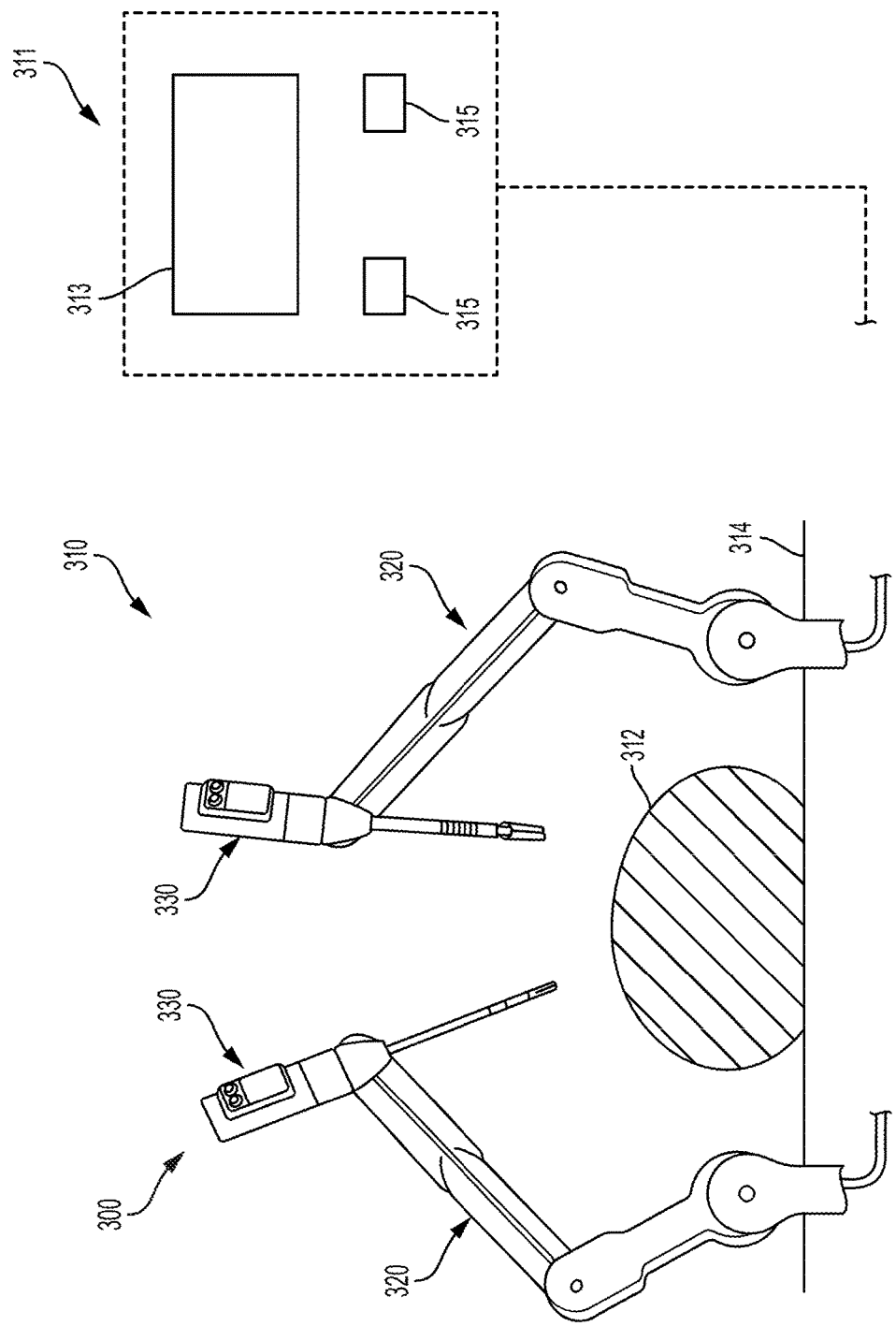
FIG. 1 illustrates a perspective view of an embodiment of a surgical robotic system that includes a patient-side portion and a user-side portion with the patient-side portion including at least one robotic arm configured to releasably couple to a tool assembly.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

In general, sterile barrier systems are provided for use with robotic surgical systems. The sterile barrier effectively isolates the sterile surgical tool and the sterile field from the remainder of the robotic surgical system. As such, the sterile barriers typically serve as the mechanical (and in some cases, electrical) interface between the surgical tool and the tool driver. As discussed below, the sterile barriers disclosed herein can accommodate surgical tools of various shapes, including cylindrical, and can accommodate surgical tools with modular shafts. Thus, the sterile barrier systems described herein allow surgical tools and tool components to be removed and replaced while the sterile barrier remains in place and intact.

The systems, devices, and methods disclosed herein can be implemented using a robotic surgical system. As will be appreciated by a person skilled in the art, electronic communication between various components of a robotic surgical system can be wired or wireless. A person skilled in the art will also appreciate that all electronic communication in the system can be wired, all electronic communication in the system can be wireless, or some portions of the system can be in wired communication and other portions of the system can be in wireless communication.

FIG. 1 is a perspective view of one embodiment of a surgical robotic system 300 that includes a patient-side portion 310 that is positioned adjacent to a patient 312, and a user-side portion 311 that is located a distance from the patient, either in the same room and/or in a remote location. The patient-side portion 310 generally includes one or more robotic arms 320 and one or more tool assemblies 330 that are configured to releasably couple to a robotic arm 320. The user-side portion 311 generally includes a vision system 313 for viewing the patient 312 and/or surgical site, and a control system 315 for controlling the movement of the robotic arms 320 and each tool assembly 330 during a surgical procedure.

The master control system 315 can have a variety of configurations and it can be located adjacent to the patient, e.g., in the operating room, remote from the patient, e.g., in a separate control room, or it can be distributed at two or more locations. For example, a dedicated system control console can be located in the operating room, and a separate console can be located in a remote location. The control system 315 can include components that enable a user to view a surgical site of a patient 312 being operated on by the patient-side portion 310 and/or to control one or more parts of the patient-side portion 310 (e.g., to perform a surgical procedure at the surgical site 312). In some embodiments, the control system 315 can also include one or more manually-operated input devices, such as a joystick, exoskeletal glove, a powered and gravity-compensated manipulator, or the like. These input devices can control teleoperated motors which, in turn, control the movement of the surgical system, including the robotic arms 320 and tool assemblies 330.

The patient-side portion can also have a variety of configurations. As depicted in FIG. 1, the patient-side portion 310 can couple to an operating table 314. However, in some embodiments, the patient-side portion 310 can be mounted to a wall, to the ceiling, to the floor, or to other operating room equipment. Further, while the patient-side portion 310 is shown as including two robotic arms 320, more or fewer robotic arms 320 may be included. Furthermore, the patient-side portion 310 can include separate robotic arms 320 mounted in various positions, such as relative to the surgical table 314 (as shown in FIG. 1). Alternatively, the patient-side portion 310 can include a single assembly that includes one or more robotic arms 320 extending therefrom.

Figure 2:
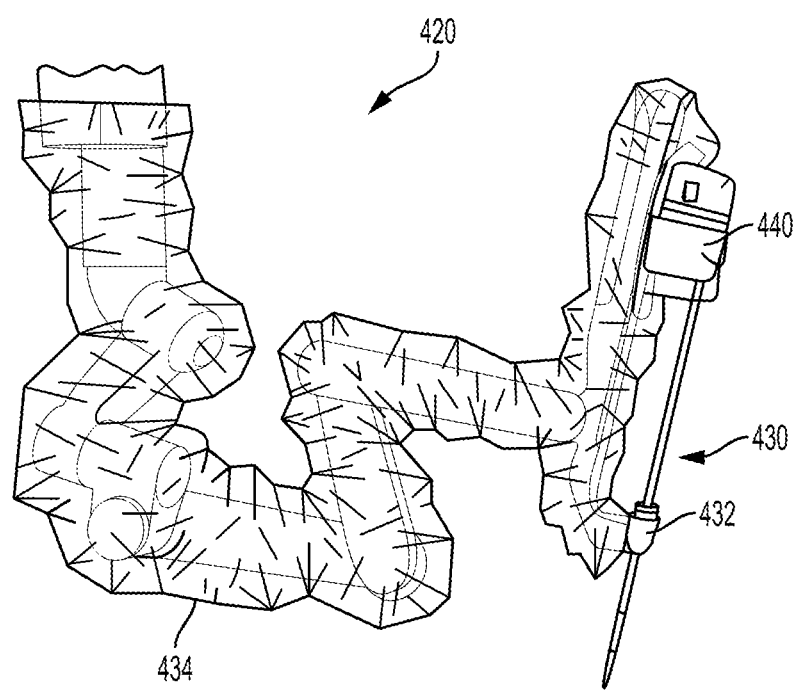
FIG. 2 illustrates an embodiment of a robotic arm and a tool assembly releasably coupled to the robotic arm.

FIG. 2 illustrates one embodiment of a robotic arm 420 and a tool assembly 430 releasably coupled to the robotic arm 420. The robotic arm 420 can support and move the associated tool assembly 430 along one or more mechanical degrees of freedom (e.g., all six Cartesian degrees of freedom, five or fewer Cartesian degrees of freedom, etc.).

The robotic arm 420 can include a tool driver 440 at a distal end of the robotic arm 420, which can assist with controlling features associated with the tool assembly 430. The robotic arm 420 can also include an entry guide 432 (e.g., a cannula mount or cannula) that can be a part of or removably coupled to the robotic arm 420, as shown in FIG. 2. A shaft 436 of the tool assembly 430 can be inserted through the entry guide 430 for insertion into a patient.

In order to provide a sterile operation area while using the surgical system, a barrier 434 can be placed between the actuating portion of the surgical system (e.g., the robotic arm 420) and the surgical instruments (e.g., the tool assembly 430). A sterile component, such as an instrument sterile adapter (ISA), can also be placed at the connecting interface between the tool assembly 430 and the robotic arm 420. The placement of an ISA between the tool assembly 430 and the robotic arm 420 can ensure a sterile coupling point for the tool assembly 430 and the robotic arm 420. This permits removal of tool assemblies 430 from the robotic arm 420 to exchange with other tool assemblies 430 during the course of a surgery without compromising the sterile surgical field.

Figure 3:
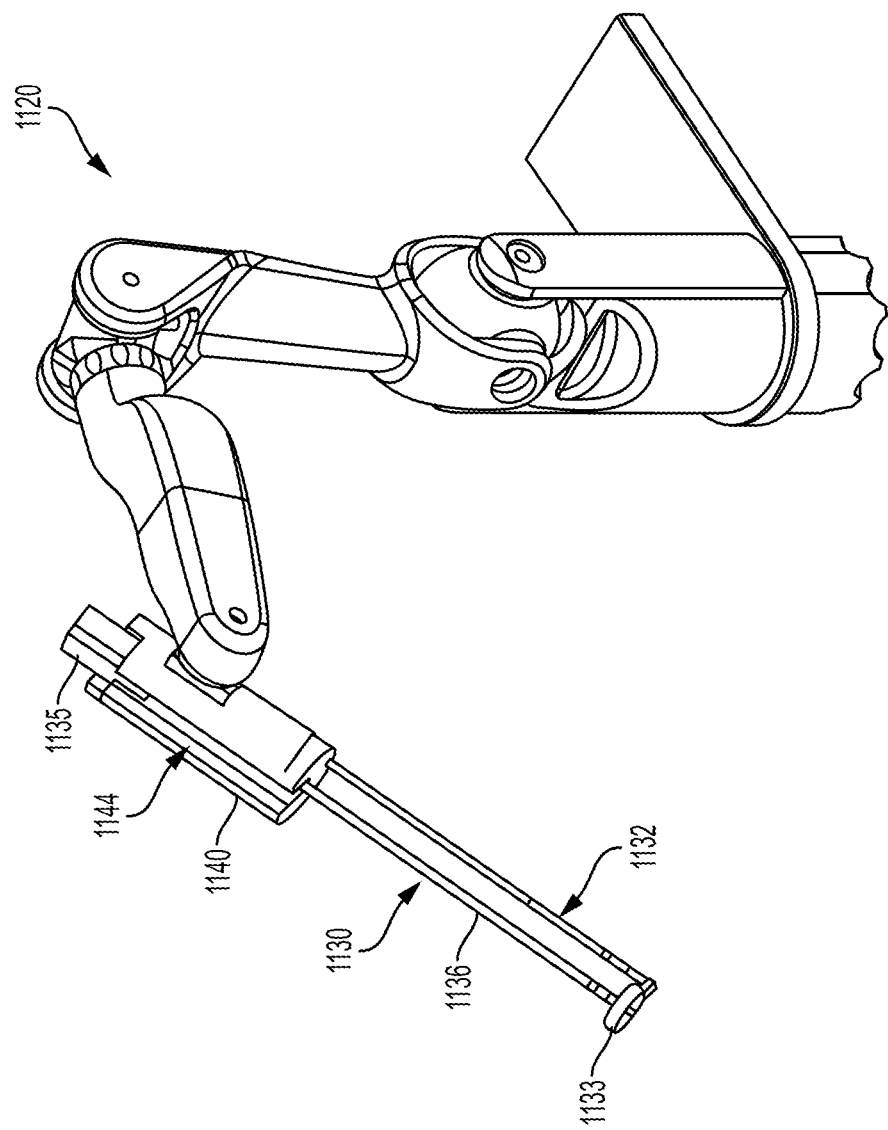
FIG. 3 illustrates an embodiment of the robotic arm of FIG. 1 having an embodiment of a tool assembly releasably coupled to the robotic arm.

FIG. 3 illustrates another embodiment of a robotic arm 1120 and a tool assembly 1130 releasably coupled to the robotic arm 1120. The robotic arm 1120 can support and move the associated tool assembly 1130 along one or more mechanical degrees of freedom (e.g., all six Cartesian degrees of freedom, five or fewer Cartesian degrees of freedom, etc.).

The robotic arm 1120 can include a tool driver 1140 at a distal end of the robotic arm 1120, which can assist with controlling features associated with the tool assembly 1130. The robotic arm 1120 can also include a movable tool guide 1132 that can retract and extend relative to the driver 1140. A shaft of the tool assembly 1130 can extend parallel to a threaded shaft of the movable tool guide 1132 and can extend through a distal end feature 1133 (e.g., a ring) of the movable tool guide 1130 and into a patient.

As described further below, in order to provide a sterile operation area while using the surgical system, a barrier (not shown in FIG. 3) can be placed between the actuating portion of the surgical system (e.g., the robotic arm 1120) and the surgical instruments (e.g., the tool assembly 1130) in the sterile surgical field. A sterile component, such as an instrument sterile adapter (ISA), can also be placed at the connecting interface between the tool assembly 1130 and the robotic arm 1120. The placement of an ISA between the tool assembly 1130 and the robotic arm 1120 can ensure a sterile coupling point for the tool assembly 1130 and the robotic arm 1120. This permits removal of tool assemblies 1130 from the robotic arm 1120 to exchange with other tool assemblies 1130 during the course of a surgery without compromising the sterile surgical field.

Figure 4:
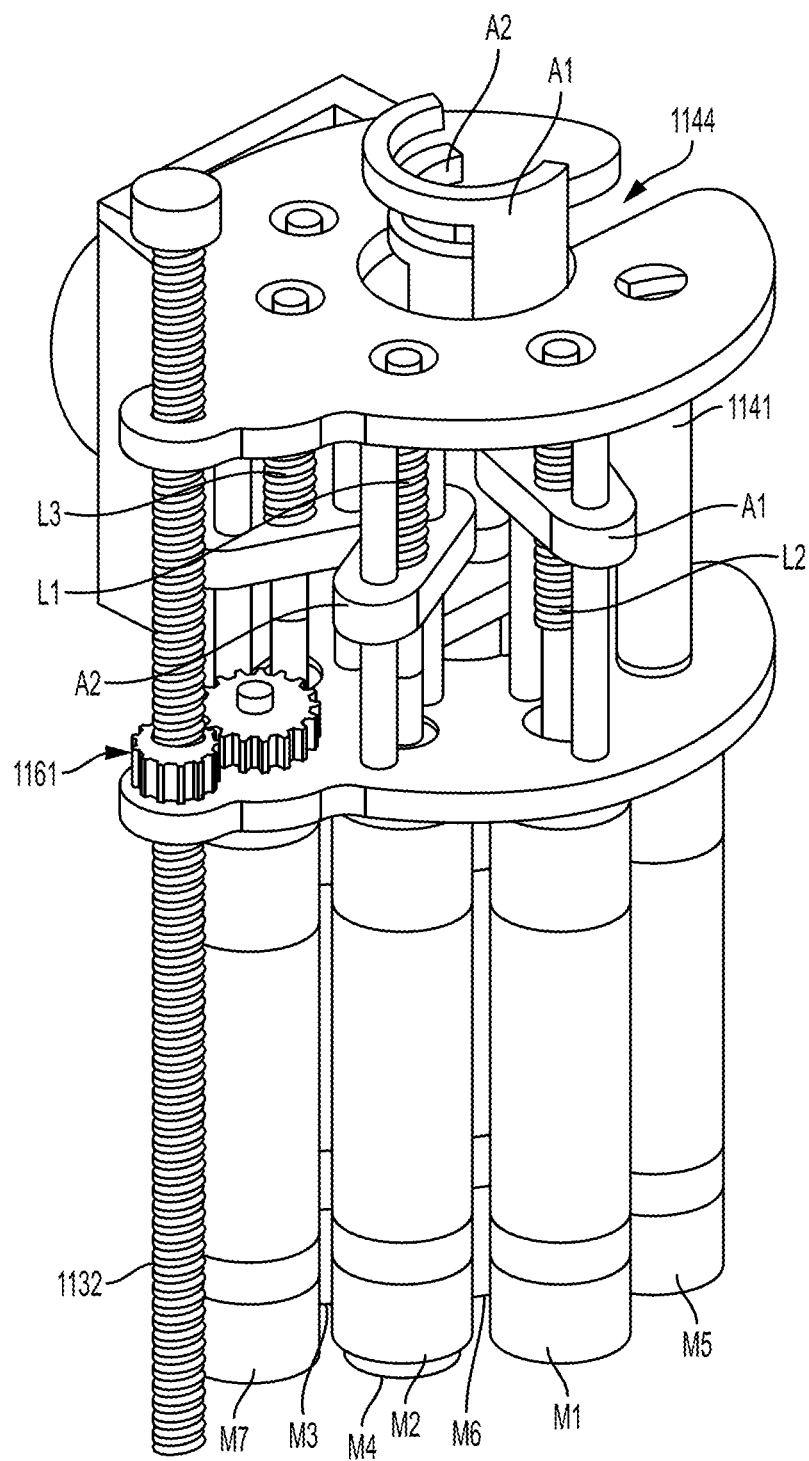
FIG. 4 illustrates a tool driver of the robotic arm of FIG. 3 having one or more motors that control a variety of movements and actions associated with the tool assembly.

FIG. 4 illustrates the tool driver 1140 in more detail. As shown, the tool driver 1140 includes one or more motors, e.g., seven motors M1-M7 are shown, that control a variety of movements and actions associated with the tool assembly 1130, as will be described in greater detail below. The driver 1140 can also include one or more lead screws (e.g., three lead screws L1, L2, and L3 are shown) that can be individually rotated by a motor and, as a result of the rotation of the lead screw, cause linear and/or rotational movement of at least one actuator (e.g., see, for example, actuators A1 and A2 shown in FIG. 4). Movement of each actuator controls the movement of driving members (e.g., gears, cables) located in the tool assembly 1130 for controlling one or more actions and movements that can be performed by the tooling assembly 1130, such as for assisting with performing a surgical operation. The actuators extend from a top end of the driver 1140 for coupling to the driving members of the tool assembly 1130 mounted on top of the tool driver 1140.

The tool assembly 1130 can be loaded from a top side of the driver 1140 with the shaft of the tool assembly 1130 being positioned in a shaft-receiving channel 1144 formed along the side of the driver 1140. The shaft-receiving channel 1144 allows the shaft, which extends along a central axis of the tool assembly 1130, to extend along a central axis of the driver 1140 when the tool assembly 1130 is coupled to the driver 1140. In other embodiments, the shaft can extend through on opening in the tool driver 1140, or the two components can mate in various other configurations.

Figure 5:
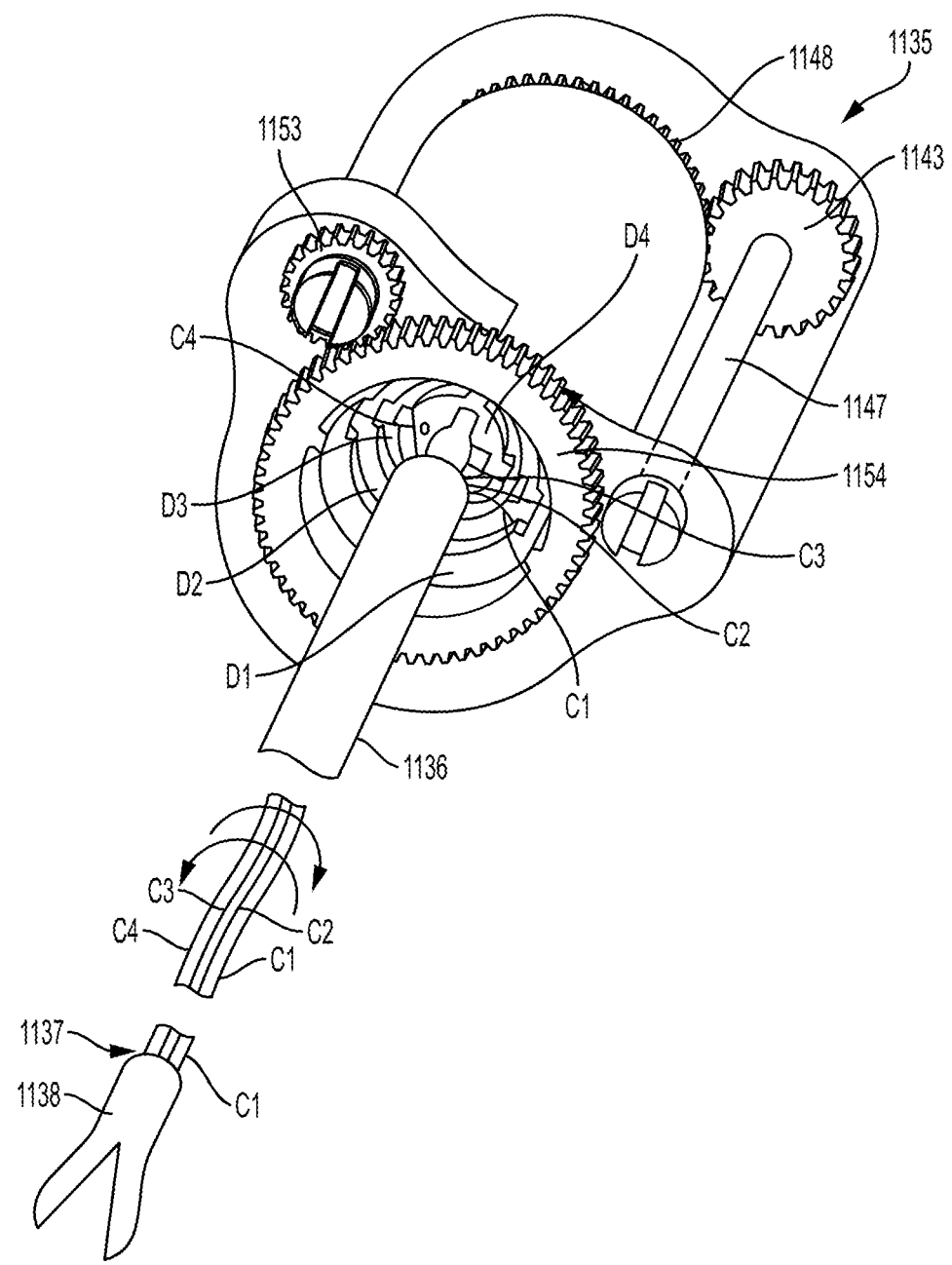
FIG. 5 illustrates a part of a puck actuation assembly contained within the puck of the tool assembly of FIG. 3.

As shown in FIGS. 3 and 5, the tool assembly 1130 includes a housing or puck 1135 coupled to a proximal end of a shaft 1136 and an end effector 1138 coupled to a distal end of the shaft 1136. The puck 1135 can include coupling features that assist with releasably coupling the puck 1135 to the tool driver 1140 of the robotic arm 1120. The puck 1135 can include driving members (e.g., gears, cables, and/or drivers) that can be directly or indirectly actuated by the one or more motors M1-M5, as will be described in greater detail below. The driving members in the puck 1135 can control the operation of various features associated with the end effector 1138 (e.g., clamping, firing, rotation, articulation, etc.), as well as control the movement of the shaft 1136 (e.g., rotation and/or articulation of the shaft).

The shaft 1136 can be releasably coupled to the puck 1135 such that the shaft 1136 can be interchangeable with other shafts. This can allow a single puck 1135 to be adaptable to various shafts 1136 having different end effectors 1138. The shaft 1136 can include actuators and connectors that extend along the shaft and assist with controlling the actuation and/or movement of the end effector 1138 and/or shaft 1136. The shaft 1136 can also include one or more joints or wrists 1137 that allow a part of the shaft 1136 or the end effector 1138 to rotate and/or articulate relative to the longitudinal axis of the shaft 1136. This can allow for fine movements and various angulation of the end effector 1138 relative to the longitudinal axis of the shaft 1136. The end effector 1138 can include any of a variety of surgical tools, such as a stapler, a clip applier, forceps, a needle driver, a cautery device, a cutting tool, a pair of jaws, an imaging device (e.g., an endoscope or ultrasound probe), or a combined device that includes a combination of two or more various tools.

FIG. 5 illustrates a part of a puck actuation assembly contained within the puck 1135. As shown in FIG. 5, the puck 1135 includes at least one driving member (e.g., four driving members D1. D2, D3, and D4 are shown) that can each become engaged with an actuator of the driver 1140 such that actuation of an actuator causes actuation of a driving member thereby controlling the operation of various features associated with the shaft 1136 and/or end effector 1138. Each driving member D1-D4 can be coupled to a proximal end of a shaft or cable (e.g., four cables C1, C2, C3, and C4 are shown). Each cable can extend from a driving member and couple to a feature associated with either the shaft 1136 or the end effector 1138 thereby controlling a function of such feature.

Figure 6:
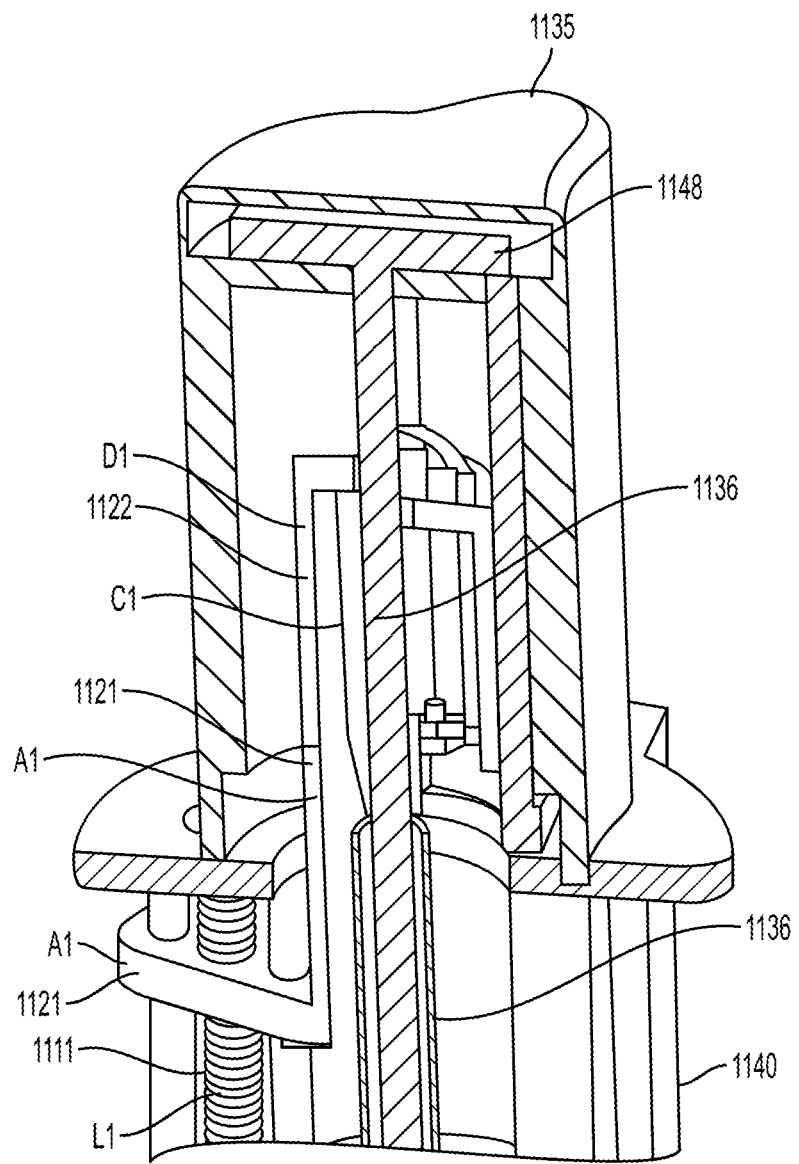
FIG. 6 illustrates the puck of FIG. 5 coupled to the driver with the actuators extending from the driver into the puck and engaging driving members.

FIG. 6 illustrates the puck 1135 coupled to the driver 1140 with the actuators extending from the driver 1140 into the puck 1135 and engaging the driving members. For example, motor M1 can cause lead screw L1 to rotate thereby causing actuator A1, which is threadably coupled to lead screw L1, to linearly advance in the proximal direction (towards and into the puck 1135). Actuator A1 can include an extension threadably coupled to the lead screw L1. The extension can be coupled to or integrated with a partial cylindrical shaft that extends along the longitudinal axis of the puck 1135 and the driver 1140. The partial cylindrical shaft of the actuator A1 can engage with driving member D1 such that when the actuator A1 is linearly advanced, the driving member D1 is caused to linearly advance in the same direction. Driving member D1 can be coupled to cable C1 such that when driving member D1 is advanced in the proximal direction, cable C1 is pulled in the proximal direction. Cable C1 extends along the shaft of the tool assembly 1130 and is operatively coupled to a part of the end effector 1138 thereby controlling a function of the end effector 1138 (e.g., opening and closing of jaws, deployment of a staple, etc.) when the cable is C1 translated in either the proximal or distal direction.

In some implementations, for example, four motors (e.g., M1-M4) can each individually control movement of a respective lead screw (e.g., L1-L4) thereby individually linearly translating a respective actuator (e.g., A1-A4) coupled thereto. Although the actuators are described as being linearly translated, the actuators can be linearly translated and/or rotationally moved as a result of actuation of a respective motor. Additional motors (e.g., motors M5 and M6) can be included in the driver 1140 for actuating various other aspects of the tool assembly 1130. For example, motor M5 can cause a first driver shaft 1141 to rotate, which is operatively coupled to a first puck shaft 1147 having a first puck gear 1143 coupled to a distal end of the first puck shaft 1147. Rotation of the first driver shaft 1141 thereby causes the first puck shaft 1147 and first puck gear 1143 to rotate. The first puck gear 1143 is engaged with a first shaft rotation gear 1148 that is caused to rotate as a result of the first puck gear 1143 rotating. The first shaft rotation gear 1148 is operatively coupled to the shaft 1136 of the tool assembly 1130 and can thereby cause rotation of the shaft 1136 and/or end effector 1138. Motor M6 can cause a second driver shaft to rotate, which is operatively coupled to a second puck gear 1153. The second puck gear 1153 is engaged with a second shaft rotation gear 1154 that is caused to rotate as a result of the second puck gear 1153 rotating. The second shaft rotation gear 1154 is also operatively coupled to the shaft 1136 and, upon rotation, provides additional torque through the shaft 1136 and for various features associated with the end effector 1138. Actuation of motor M7 can cause shaft gears 1161 to rotate, thereby causing the threaded shaft of the movable tool guide 1132 to linearly translate.

As mentioned above, during a surgical procedure using a robotic surgical system, it is desirable to separate a sterile surgical tool environment from a non-sterile environment in which other components of the robotic surgical system are located. Thus, in some embodiments, a sterile barrier is provided that effectively isolates the sterile surgical tool from the remainder of the robotic surgical system. The sterile barrier can have various shapes and it can be formed in multiple planes.

Figure 7:
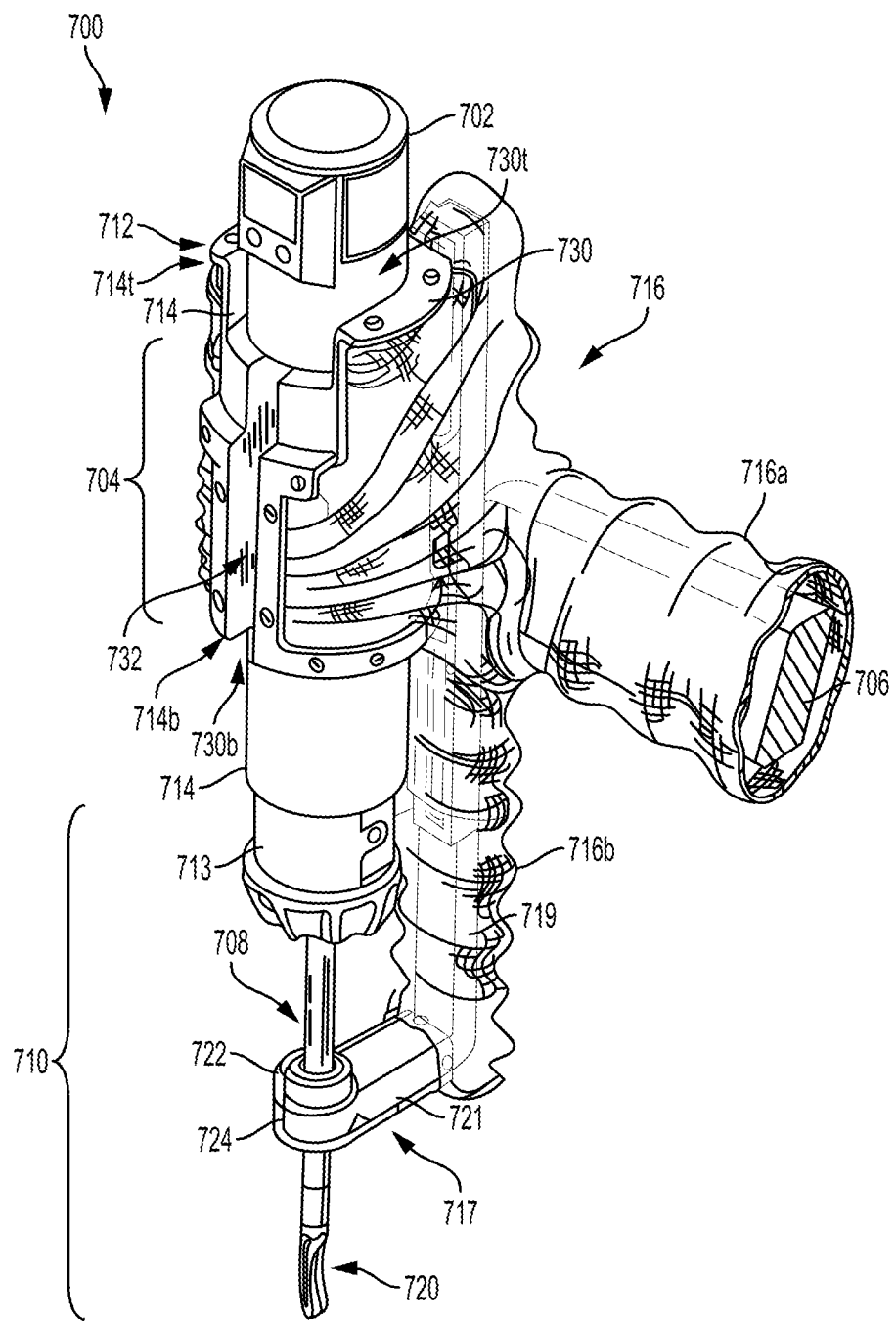
FIG. 7 illustrates an embodiment of a surgical tool assembly having a sterile barrier.

FIG. 7 illustrates a surgical tool assembly 700 of a robotic surgical system that includes a sterile barrier in accordance with the described techniques. As shown in FIG. 7, the surgical tool assembly 700 includes a puck portion or a tool housing 702 configured to be releasably coupled with a tool driver 704 (not visible, as discussed below) and reversibly coupled to a robotic surgical arm 706, which is only partially shown in FIG. 7. The tool assembly 700 includes a surgical tool attachment 710 that is removably and replaceably coupled to tool driver 704 and that has an end effector 720 coupled to a distal end of an elongate shaft 708. In the illustrated example, the surgical tool attachment 710 is coupled to the tool housing 702 and the tool driver 704 via an adapter 711. The adapter 711 can be a modular shaft adapter and the elongate shaft 708 with the end effector 720 at its distal end can be a modular shaft that can be replaced by other modular shafts. Thus, the adapter 711 can provide for the attachment to tool assembly 700 of various tool drivers and various surgical tool attachments. The adapter 711 can be coupled to the elongate shaft 708 via an interface 713, as shown in FIG. 7. As also shown in FIG. 7, the robotic surgical arm 706 includes (or is coupled to) a movable tool guide 719 that couples to a trocar 722. The trocar 722 can be reversibly mated to a trocar holding feature 724 (e.g., a ring or other feature) of the tool guide 719. The tool guide 719 is configured to hold the trocar to allow the shaft of the surgical tool assembly 700, which extends generally parallel to a threaded shaft of the tool guide 719, to be advanced through and retracted from the trocar 722.

In the example of FIG. 7, the surgical tool assembly 810, including the adapter 711 and the surgical tool attachment 710, is sterile, whereas other components of the robotic surgical system are non-sterile. The sterile barrier 712 is used to create a sterile field for the non-sterile components.

The sterile barrier 712 can have various configurations. In the illustrated example, the sterile barrier 712 includes a substantially rigid housing 714 having attached thereto a sterile flexible fabric 716. The sterile barrier 712 defines a boundary between a sterile field and a non-sterile field. In this example, both the robotic surgical arm 706 and tool driver 720 are disposed in the non-sterile field and thus need be separated from the sterile field with a sterile barrier. The sterile barrier 712 is coupled to at least one of the tool driver and the robotic arm using suitable mechanical and electrical connection(s). For example, the sterile barrier 712 can have at least one electrical contact configured to operably mate with at least one electrical contact on at least one of the tool driver 720 and the robotic arm 706, as discussed in more detail below.

FIG. 7 further illustrates that housing 714 of the sterile barrier 712 is configured to be removably attached to the tool driver 720 such that the tool driver is obscured in FIG. 7 because of its having the housing 714 with the sterile flexible fabric 716 at least partially therearound. The sterile barrier 712 has a complex shape that extends in more than one plane. Such a configuration allows the sterile barrier 712 to removably and replaceably receive the surgical tool assembly 700. Furthermore, the configuration of the sterile barrier 712 and some of its features allow it to remain in place and intact when it is in use.

The housing 714 of the sterile barrier 712 can have various shapes. For example, as shown in FIG. 7, the housing 714 can be generally cylindrically shaped elongate member having a c-shaped cross section. The housing 714 serves as a frame to enable the sterile barrier 712 to be removably attached to tool driver 720 and to support the flexible sterile fabric 716. The housing 714 extends from a top or proximal portion $714_t$ to a bottom or distal portion $714_b$. The top portion $714_t$ includes an annular flange 730. The housing 714 further includes top and bottom openings $730_t$, $730_b$ that enable a surgical tool, such as the surgical tool assembly 700 to pass therethrough. Further, the housing 714 can include a longitudinal slot 732 that separates the housing into left and right sections. As shown in FIG. 7, the slot 732 can have a larger dimension at a top portion thereof than at a bottom portion thereof. The slot 732 facilitates manipulation, including the removability and replaceability of the surgical tool within the tool driver without having to remove or affect sterile barrier 712. It should be appreciated that the housing 714 can have other shapes. For example, it can be semi-circular, circular, or it can have any other shape, including irregular.

A person skilled in the art will appreciate that the flexible sterile fabric 716 can be attached to housing 714 by any suitable manner, including by welding and/or by the use of fastening elements such as grommets.

The sterile flexible fabric 716 extending from the housing 714 of the sterile barrier 712 can have various shapes and sizes that allow the sterile flexible fabric 716 to define a sterile side on which the surgical tool is disposed. Thus, as shown in the example of FIG. 7, the sterile flexible fabric 716 is formed in more than one plane. Specifically, as shown, the flexible sterile fabric 716 extends from the housing 714 so as to provide a sterile pocket or opening into which at least a portion of the surgical tool assembly 700 is inserted. From its attachment points along the housing 714, the sterile flexible fabric 716 enshrouds the tool driver 720 and the robotic arm 706, thereby defining a sterile field.

The flexible sterile fabric 716 can be shaped such that it has features for covering various components. Thus, in FIG. 7, the flexible sterile fabric 716 has a first sterile sleeve 716a (partially shown) configured to cover the robotic arm 706, and a second sterile sleeve 716b configured to cover the tool guide 719 coupled to the robotic arm 706 via a coupling arm 721 (the tool guide 719 can be part of the robotic arm 706). The first and second sterile sleeves 716a. 716b can be removably attached to the robotic arm 706 and the tool guide 719 in various ways (e.g., using suitable fastening elements). Regardless of the way in which the first and second sterile sleeves 716a. 716b are coupled to the robotic arm 706 and the tool guide 719, the sleeves 716a, 716b are shaped and sized such that they do not obstruct movements of the surgical robotic arm 706.

It should be appreciated that the flexible sterile fabric 716 is shown in FIG. 7 by way of example only, as a flexible sterile fabric of a sterile barrier described herein can have one sleeve, two sleeves, or more than two sleeves, and/or other features that enshroud non-sterile components of the robotic surgical system to create a sterile barrier. For example, the sterile barrier 712 additionally has a sterile barrier cover 717 covering the trocar 722 and the trocar holding feature 724, as shown in FIG. 7. The sterile barrier cover 717 extends over the coupling arm 721 such that the sterile field created by the second sleeve 716b is not interrupted. The sterile barrier cover 717 can be a molded feature formed from a suitable material. A person skilled in the art will understand that the flexible sterile fabric 716, the sterile barrier cover 717, and any other features that can be coupled to the housing 714, and can be made of any suitable barrier materials (including, as in this example, different materials) that are durable and able to be sterilized. Various polymeric films or sheets, such as polyethylene, polypropylene, polytrifluoroethylene, latex, and neopene, can be useful barrier materials, and the polymeric material can be elastic or inelastic.

Figure 8:
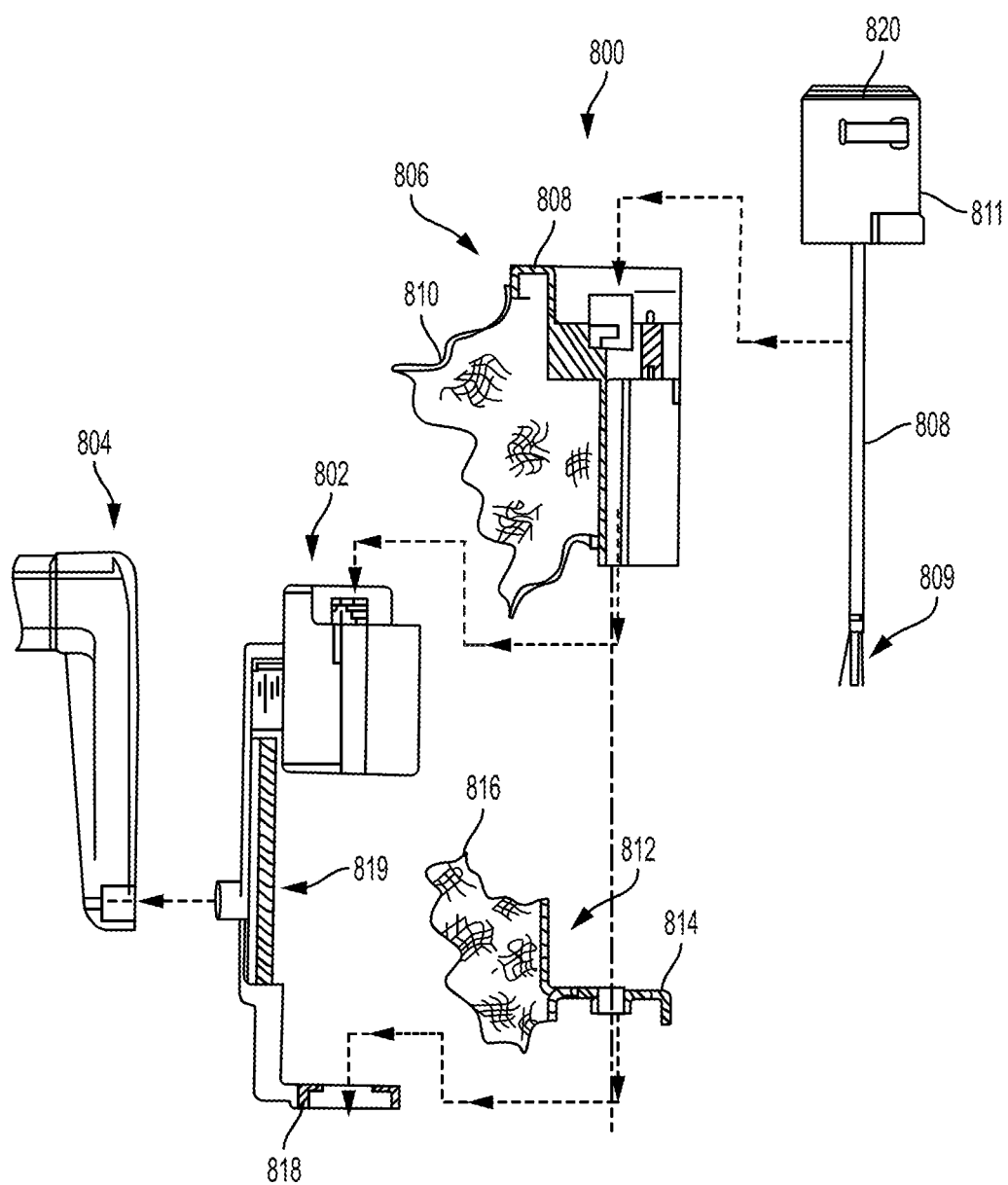
FIG. 8 illustrates an exploded view of a portion of a robotic surgical system including a sterile barrier.

FIG. 8 illustrates an exploded view of a surgical tool assembly 800, which can be similar to the surgical tool assembly 700 in FIG. 7. The surgical tool assembly 800 includes a sterile barrier system. As shown in FIG. 8, a tool driver 802 is coupled (reversibly or irreversibly) to a movable tool guide 819 and is removably attached to a surgical robotic arm 804. A sterile barrier 806 is removably attached to the tool driver 802 by attaching a housing 808 with its associated flexible sterile fabric 810 to the tool driver 802. A person skilled in the art will appreciate that a variety of mechanical connection systems, including snap fit, interference fit, dovetail, hook and loop, straps and bands, latches, etc. can be used to removably mate the sterile barrier 806 to the tool driver 802. Similarly, a lower sterile barrier 812, including a lower barrier housing 814 and a lower flexible sterile fabric 816 can be removably mated to a trocar holding feature 818 and a trocar (not shown). Although only portions of the flexible sterile fabrics 810, 816 are shown, it is understood that the sterile fabrics enshroud non-sterile components of the system such as the tool driver 802 and the robotic arm 804, thus creating a sterile barrier.

Similar to the description above with respect to FIG. 7, a surgical tool 820 can be removably and replaceably inserted within the tool driver 802, and into the sterile space defined by the sterile barrier. However, the surgical tool 820 can be different from the surgical tool assembly in FIG. 7 in that the surgical tool 820 may not include an adapter, but rather an elongate shaft 808 of the tool 820 having an end effector 809 at a distal end thereof can be coupled directly to a puck portion or a tool housing 811. However, as a person skilled in the art will appreciate, the surgical tool 820 can have any other configurations, including a configuration similar to that in FIG. 7.

As mentioned above and as discussed below, in addition to the mechanical connection that the sterile barrier provides between the tool and the tool driver, the sterile barrier also provides an electrical connection between the tool and the tool driver and associated components of the system.

Figure 9:
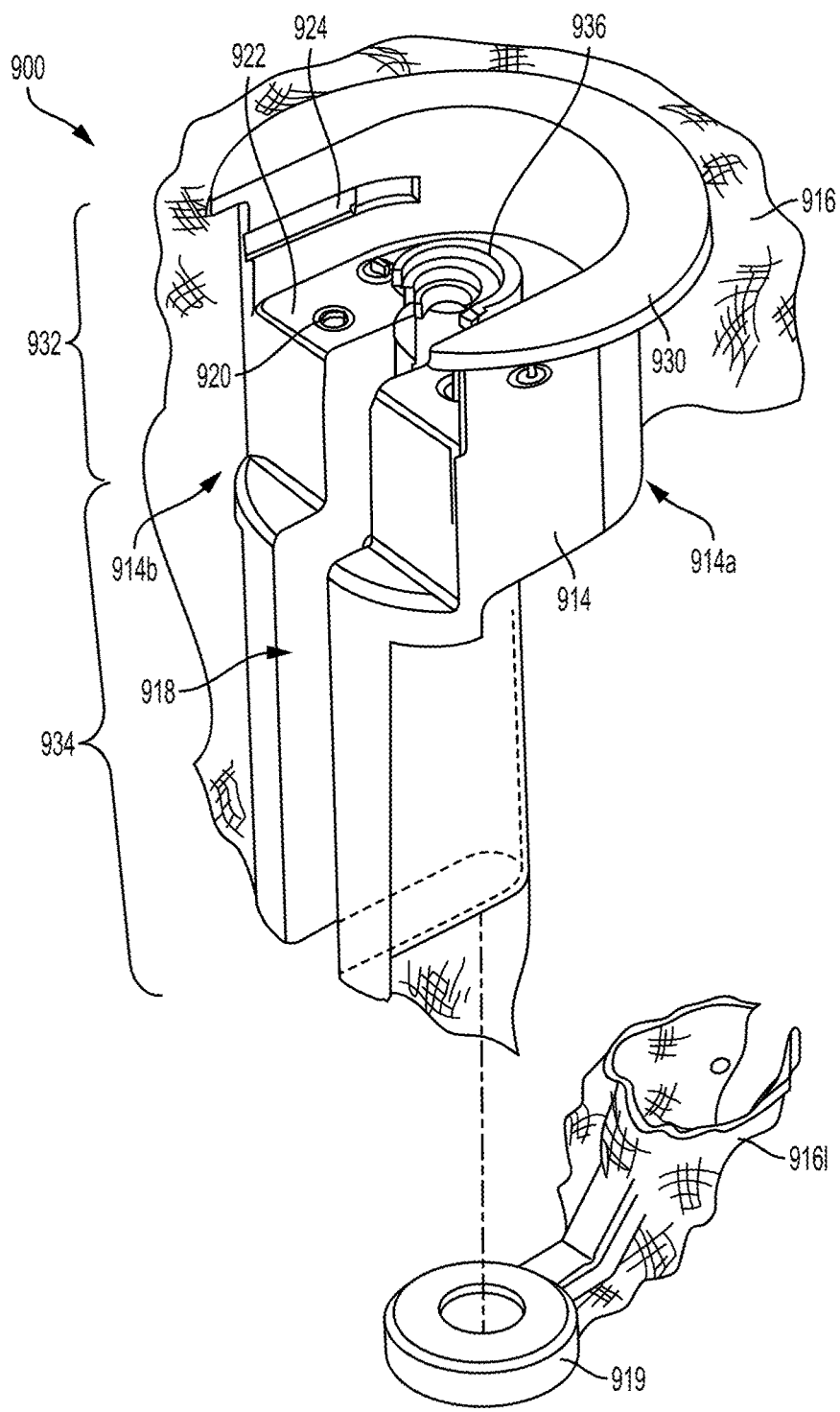
FIG. 9 illustrates a perspective view of portions of a sterile barrier between a tool and a tool driver of a surgical tool assembly.

FIG. 9 illustrates an example of a sterile barrier 900 having a housing 914 having a flexible sterile fabric 916 (partially shown) extending therefrom. As shown, similar to the examples in FIGS. 7 and 8, a lower portion 916l of the flexible sterile fabric 916 is configured to cover at least in part a movable tool guide having a trocar holding ring 919. The housing 914 is a substantially rigid, generally cylindrical elongate member having a substantially c-shaped cross-section. The housing 914 has a first side 914a that is configured to be received within and mate with an opening in a tool driver and a second side 914b opposite the first side 914b, having a housing opening 918 formed therein that is configured to receive a surgical tool.

As shown in FIG. 9, the housing 914 is formed of an annular rim 930, a first section 932, and a second section 934. The annular rim 930 that is configured to attach the sterile flexible fabric 916 extending therefrom such that an exterior portion of the housing 914 defines the sterile side and an interior portion of the housing 914 defines the non-sterile side. The first section 932, has on its inner c-shaped (or u-shaped) surface 922 that is offset from the annular rim 930, at least one electrical contact 920 to operably mate with at least one electrical contact (not shown) on at least one of a tool driver and a robotic arm. As shown in FIG. 9, the first section 932 also has, on its inner wall extending between the rim 930 and the surface 922, slots 924 (one of which is shown) configured to mate with a puck portion or housing of a surgical tool. As shown in FIG. 9, the second section 934 has a nominal diameter less than the first section 932 to receive a shaft of the surgical tool. The shaft can be an interchangeable shaft.

Figure 10:
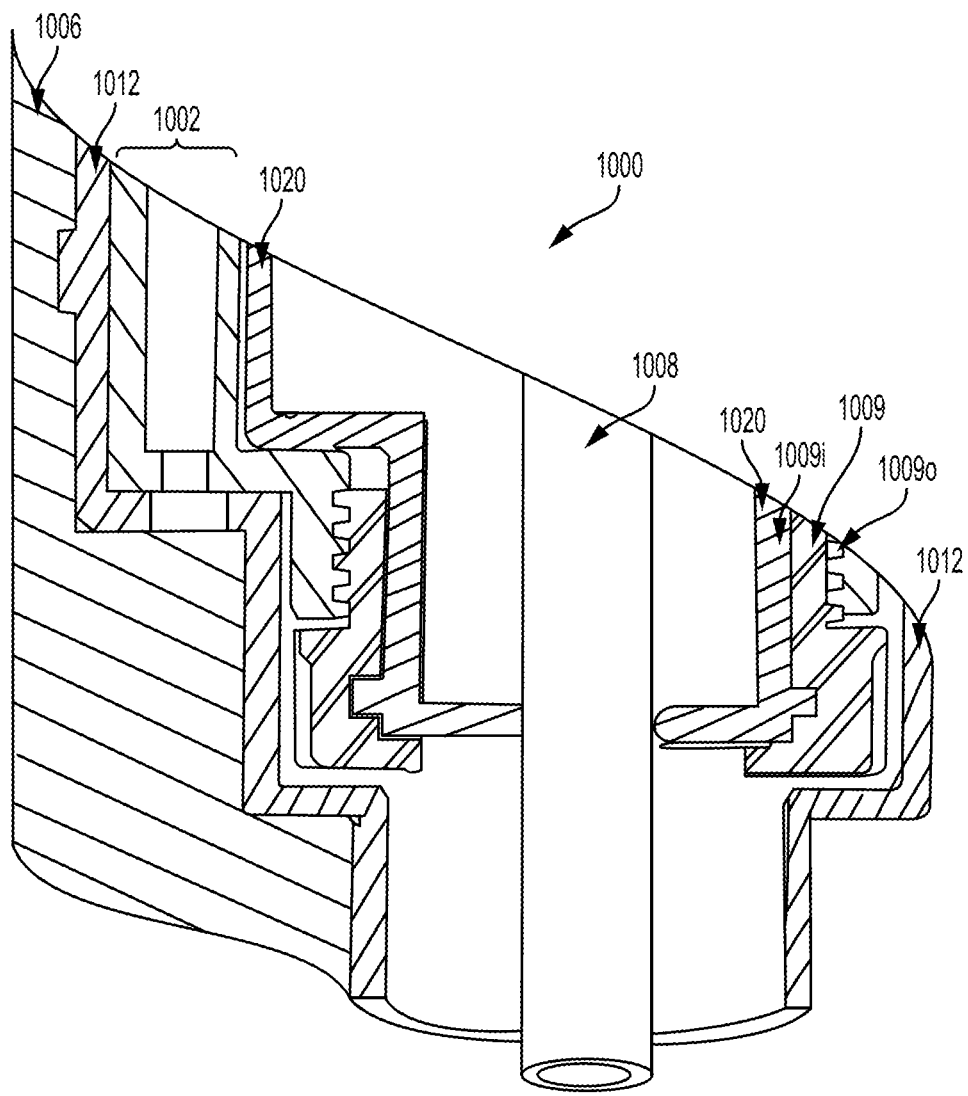
FIG. 10 illustrates a cross-sectional view of the sterile barrier assembly of FIG. 9 releasably coupled to a robotic arm.

FIG. 10 illustrates a cross-sectional view of an example of a portion of a surgical tool assembly 1000 having a sterile barrier. A tool driver 1020 is at least partially inserted into to a puck or housing 1002 of the surgical tool assembly 1000 and is coupled to the housing 1002 via coupling feature 1009, such as, e.g., a ring or other feature. The coupling feature 1009 has an inner surface 1009i configured to mate with the tool driver 1020 and an outer surface 1009o configured to mate with a portion of the surgical tool, such as the housing 1002.

An elongate shaft 1008 coupled to the housing 1002 and having an end effector at a distal end thereof (not shown) extends at least partially through the tool driver 1020 and the housing 1002. A sterile barrier 1012 creates a sterile field for non-sterile components of the tool assembly 1000, such as the tool driver 1020 and a robotic arm 1006. The sterile barrier 1012 can have a configuration similar to, for example, the sterile barrier 912 in FIG. 9. The sterile barrier 1012 can have a flexible sterile fabric extending from a housing of the sterile barrier, and any other feature(s) (e.g., a lower sterile barrier portion, one or more molded portions, etc.).

Figure 11:
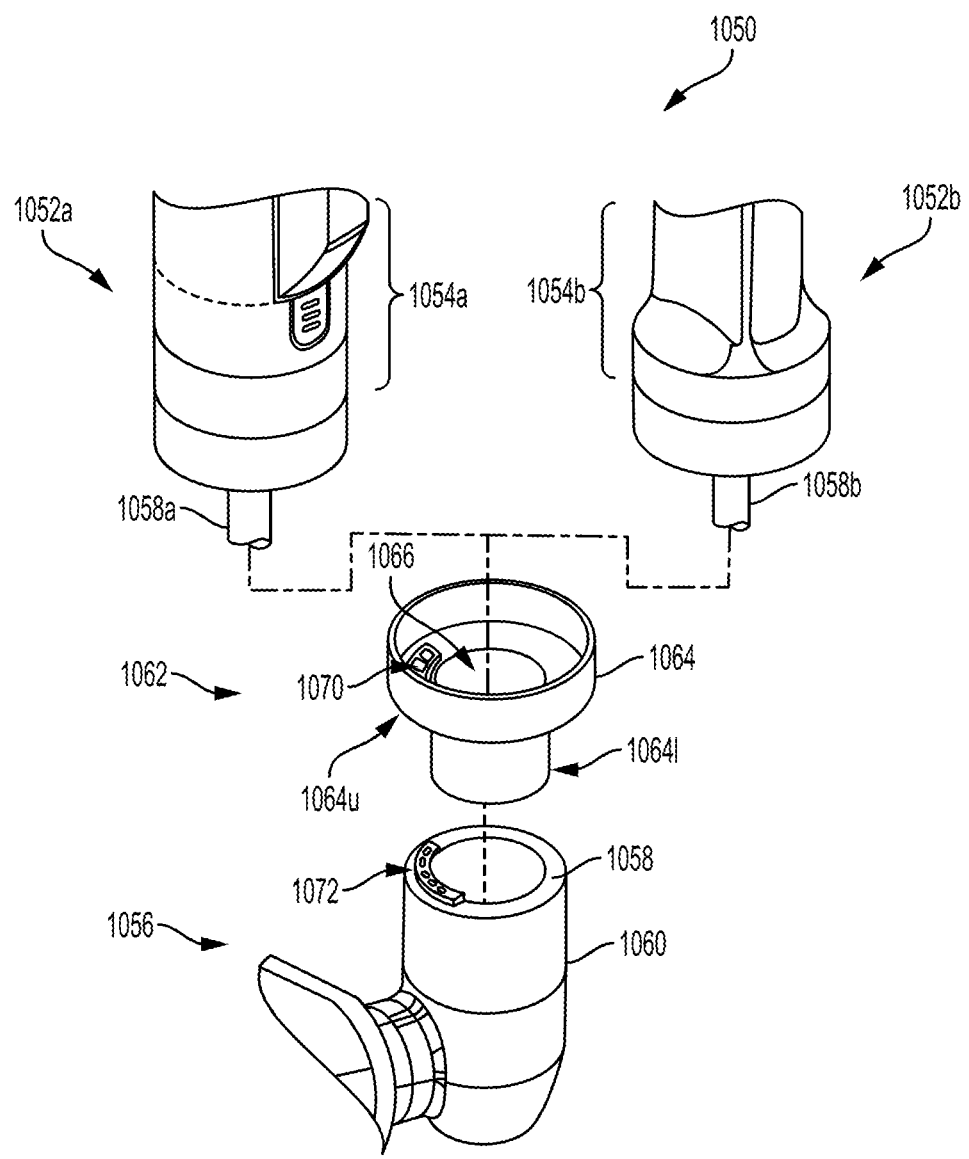
FIG. 11 illustrates an exploded view of an embodiment of a modular tool assembly releasably coupled to a robotic arm.

FIG. 11 illustrates another example of a portion of a surgical tool assembly 1050 (in exploded view) having a sterile barrier assembly. As shown, the tool assembly 1050 has a sterile barrier assembly 1062 in the form of an adapter that allows tool drivers coupled to surgical tool attachments of various types to be coupled to a robotic arm 1056. Thus, in some embodiments, the surgical tool assembly 1050 can be in the form of a kit having the adapter and various tool attachments.

The sterile barrier assembly 1062 can have various configurations. In this example, as shown in FIG. 11, the sterile barrier assembly 1062 includes a cylindrical housing 1064 having an upper or proximal portion 1064u that has a greater diameter than a lower or distal portion 1064l. The housing 1064 has an opening 1066 extending therethrough and it is configured to seat a tool driver operatively coupled to a modular shaft that is received through the opening 1066. The sterile barrier assembly 1062 can have a sterile flexible fabric (not shown) of any suitable configuration extending from the housing 1064 and coupled thereto. At least a portion of such sterile flexible fabric can be in the form of a sleeve (or a bag) configured to enshroud at least a portion of the robotic arm 1056.

The sterile barrier assembly 1062 functions as an adapter and it is thus configured to be coupled to a tool driver 1054a of a surgical tool attachment 1052a or to a tool driver 1054b of a surgical tool attachment 1052b. In this example, the tool driver 1054a, coupled to a modular shaft 1058a having an end effector (not shown) at a distal end thereof, can include, for example, an ultrasonic transducer coupled to an end effector component (e.g., a waveguide) to supply ultrasonic energy to the end effector's jaws. In this way, the end effector of the surgical tool 1052a can apply ultrasonic energy to blood vessels and tissue to cauterize, seal, or otherwise treat them. The tool driver 1054b can have a configuration different from that of the tool driver 1054a. For example, the tool driver 1054a can be configured to drive an end effector (not shown) that has opposed jaws configured to clamp tissue therebetween and apply surgical staples to the tissue. The tool driver 1054a is coupled to such end effector via a modular shaft 1058b. However, it should be appreciated that the sterile barrier assembly 1062 can be configured to couple to various surgical tool attachments having tool drivers and modular shafts of any types. Non-limiting examples of such surgical tool attachments include tools with a combination shaft including an ultrasonic shaft and radio frequency shaft, a radio frequency shaft, a shaft coupled to a linear stapler, a shaft coupled to a circular stapler, a shaft coupled to a clip applier, or any other type of modular shaft having any other end effector or other device coupled thereto. A tool driver can operatively couple to various types of modular shafts.

In the example illustrated in FIG. 11, the sterile barrier assembly 1062 acts as a sterile electrical interface between the tool driver and the robotic arm, with the interface defining a non-sterile side and a sterile side. The sterile barrier assembly 1062 defines the non-sterile sterile side such that the tool driver (e.g., the tool driver 1052a, tool driver 1052b, or any other tool driver that can be removably and replaceably coupled to the arm 1056) is on the non-sterile-side. A surgical tool, or tool attachment, (e.g., the surgical tool 1052a, 1052b, or any other tool) can be mounted within the sterile barrier assembly 1062 such that the surgical tool is on the sterile side.

The surgical tool can be operably connected to and in electrical communication with the sterile barrier assembly 1062 and the robotic arm 1056. Thus, as shown in FIG. 11, the housing 1064 of the sterile barrier assembly 1062 has electrical contacts 1070 formed on a distal-most (or bottom) outer wall of the upper housing portion 1064a that faces the arm 1056. The electrical contacts 1070 (partially shown) are configured to operably mate with complementary electrical contacts 1072 formed on a top surface of 1058 of a rim of a coupling portion 1060 of the robotic arm 1056.

The electrical contacts 1070, 1072 mate when an opening in the robotic arm's coupling portion 1060 receives therein the lower portion 10641 of the housing 1064 of the sterile barrier assembly 1062. It should be appreciated that six electrical contacts 1072 are shown by way of example only, as any number of electrical contacts of a suitable type can be formed on the robotic arm and the sterile barrier assembly. The sterile barrier assembly 1062 can also be reversibly coupled to the robotic arm 1058 using a suitable mechanical coupling mechanism, such as, e.g., a coupling ring or other feature, and those noted above). Furthermore, the sterile barrier assembly 1062 can be configured to electrically and mechanically mate with a surgical tool driver. For example, one or more electrical contacts (not shown) can be formed on the tool driver to mate with complementary electrical contacts on the robotic arm.

Regardless of the specific type of electrical and mechanical connections formed between the sterile barrier assembly and the tool driver and the robotic arm, in at least some implementations, a surgical tool attachment (also referred to as a "surgical tool"), can be removed from the sterile environment and remounted such that the sterile environment provided by the sterile barrier assembly is maintained. The removed surgical tool can also be replaced with a second surgical tool while maintaining the sterile environment.

Figure 12:
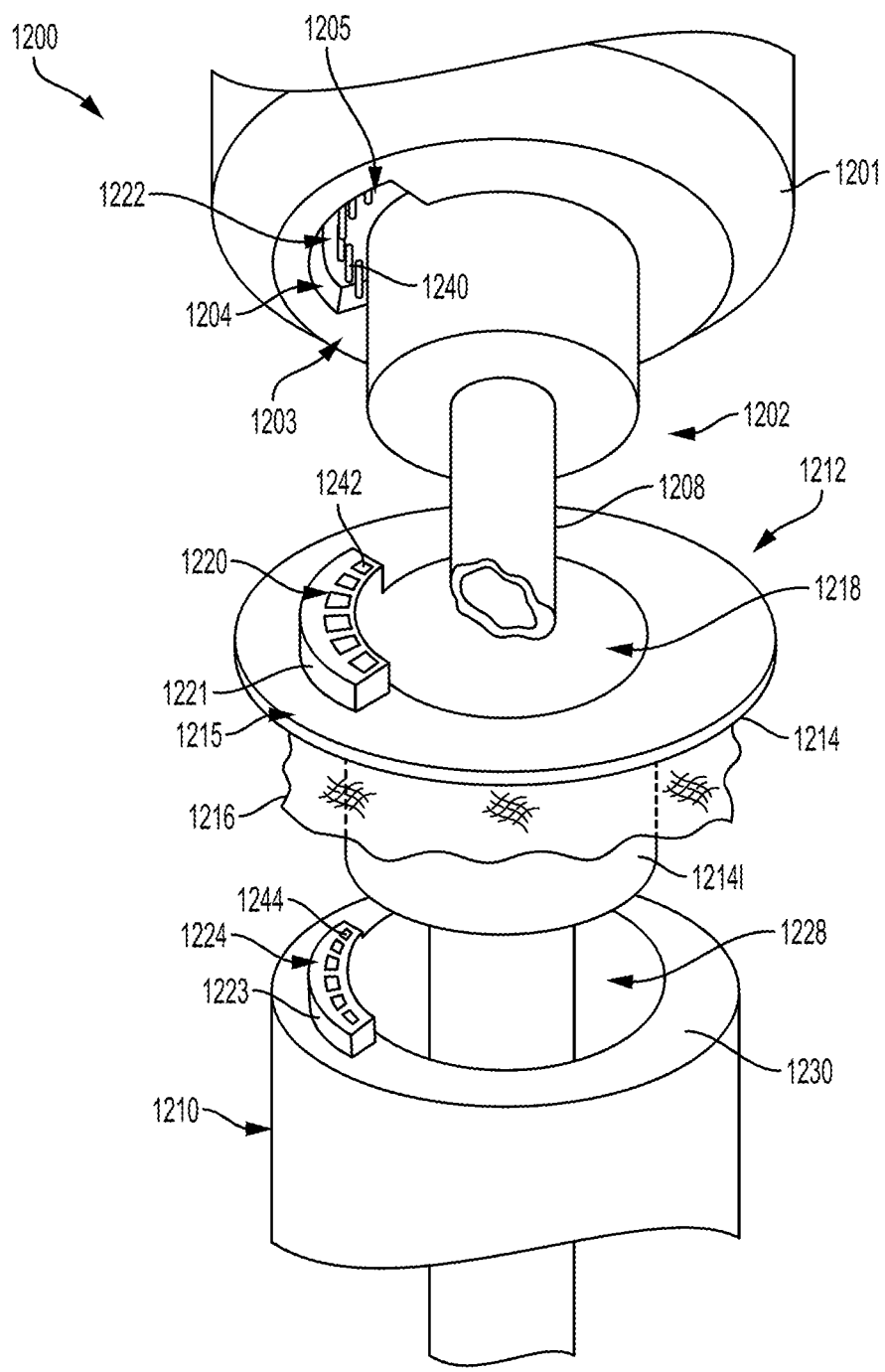
FIG. 12 illustrates the modular tool assembly of FIG. 11 having a sterile barrier between the tool and the tool driver.

FIG. 12 illustrates another example of a surgical tool assembly 1200 including a sterile barrier assembly 1212 providing a sterile electrical interface between a tool driver and a robotic arm. As shown in FIG. 12, the surgical tool assembly 1200 includes a puck or tool housing 1201 having a tool driver 1204 (only partially shown) inserted thereto. For example, the driver 1204 can be coupled to the housing similar to a manner as shown for the tool driver 1010 and the housing 1002 in FIG. 10. It should be appreciated, however, that in some embodiments the tool driver can be coupled to the housing such that only a small portion of the tool driver extends through the housing. In FIG. 12, the tool driver 1204 is coupled to a surgical tool attachment or a surgical tool 1202 and configured to couple with a robotic arm 1210 via a sterile barrier assembly 1212 in the form of an adapter. The surgical tool 1202 has a shaft 1208 having an end effector (not shown) at a distal end thereof. The shaft 1208 can be, for example, a modular shaft. The tool driver 1204 can have various configurations and it can be coupled to shafts of various types.

The sterile barrier assembly 1212 also can have various configurations. In the illustrated example, the sterile barrier assembly 1212 has a substantially rigid cylindrical housing 1214 having a sterile flexible fabric 1216 extending therefrom. The flexible fabric 1216 (partially shown) can have any suitable configurations and it can enshroud the robotic arm 1210, which can also have various configurations. As shown, the housing 1214 has an upper or proximal portion in the form of a flange 1215 and a lower or distal portion 12141 having a diameter less than that of the flange 1215. The housing 1214 has an opening 1218 configured to receive the tool 1202 therethrough. The distal portion 12141 of the housing 1214 is configured to be seated within an opening 1228 formed in the arm 1210.

FIG. 12 illustrates that the sterile barrier assembly 1212 acts as a sterile electrical interface between the tool driver and the robotic arm. Specifically, as shown, a top surface of the sterile barrier flange 1215 has a plurality of electrical contact paths or windows 1220 formed on a base 1221 raised above the surface of the flange 1215. The windows 1220 are configured to form a sealing interface between electrical contacts 1222 formed on a bottom or distal surface 1203 of the tool driver 1204, a portion of which is exposed through an opening or cavity 1205 in the bottom of the housing 1201, and complementary electrical contacts 1224 formed on the robotic arm 1210. In this example, the electrical contacts 1222 are in the form of pin contacts that are configured to penetrate and extend through the electrical contact windows 1220 to mate with the electrical contacts 1224. In this example, each contact pin of the electrical contacts 1222 can pass through a respective opening or window in the electrical contact windows 1220. For example, a contact pin 1240 of the electrical contacts 1222 can pass through an opening 1242 the electrical contact windows 1220 to mate with a contact 1244 from the electrical contacts 1224.

The electrical contacts 1224 can be of any suitable type such as, for example, contacts formed from an electroactive polymer. The cavity 1205 formed in the distal surface 1203 of the housing 1201 can be shaped and sized to sealingly fit therein the base 1221 with the electrical contact windows 1220. In this way, when the tool 1202 is inserted through the opening 1218 in the sterile barrier assembly 1212 and through the opening 1228 in the robotic arm 1210, the base 1221 is disposed within the cavity 1205 such that each pin of the electrical contact 1222 extend through the corresponding window of the electrical contact windows 1220. When the tool 1202 penetrates through the sterile barrier assembly 1212 and the arm 1210, the pins of the electrical contact 1222 extend through the windows 1220 such that the pins mate with the complementary electrical contacts 1224. As shown in FIG. 12, the electrical contacts 1224 are formed on a base 1223 having its upper surface offset from a surface of a rim 1230 of the arm 1210. Thus, the base 1223 with the electrical contacts 1224 can fit within the base 1221 on the sterile barrier 1212. In this way, the flange 1215 with the contact windows forms a sterile electrical barrier such that the housing 1201 with the tool driver 1204 is positioned on a non-sterile side and the tool 1202 with the shaft 1202 that extend through the housing 1214 are disposed on the sterile side.

It should be appreciated that six electrical contacts 1222 and six electrical contacts 1224 are shown by way of example only, as any number of electrical contacts can be formed (e.g., less than six or greater than six). The electrical contact connection between the tool driver 1204 and the robotic arm 1210 through the sterile barrier assembly 1212 allows maintaining the sterile environment even if the surgical tool 1202 penetrating the sterile barrier assembly 1212 is moved distally and proximally within at least a portion of the sterile environment. Thus, the tool 1202 can be removed from the sterile barrier assembly 1212 and it can be remounted or replaced with another surgical tool while maintaining the sterile environment.

It should be appreciated that, in some implementations, the sterile barrier assembly 1212 can additionally or alternatively include a plurality of electrical contacts that can operably mate with electrical contacts on one or both of the tool driver and the robotic arm.

Figure 13A:
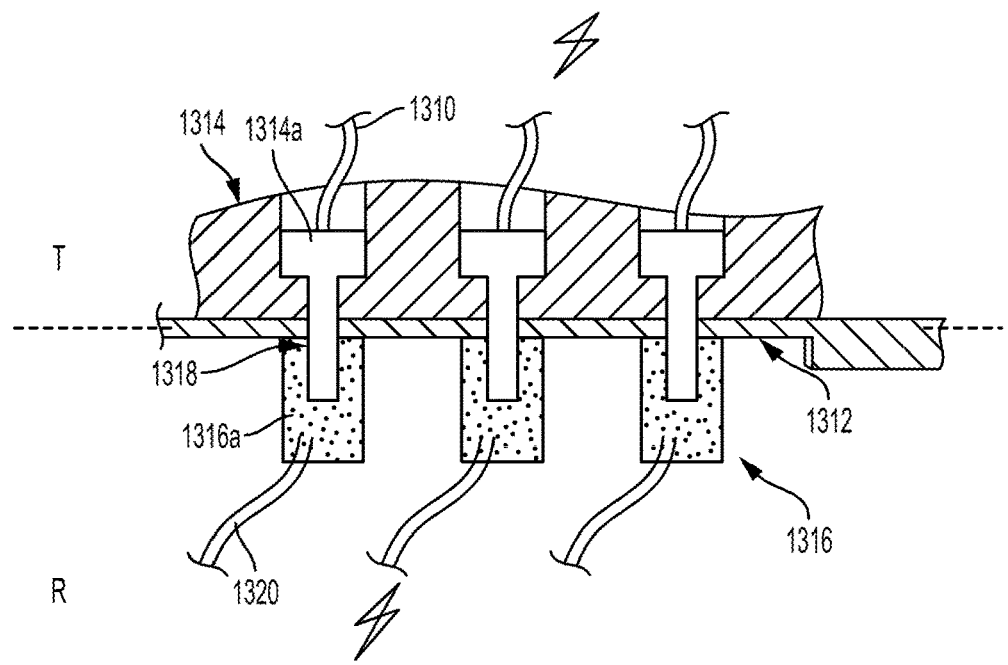
FIG. 13A illustrates an embodiment of an electrical connection formed in a sterile barrier in a surgical tool assembly.
Figure 13B:
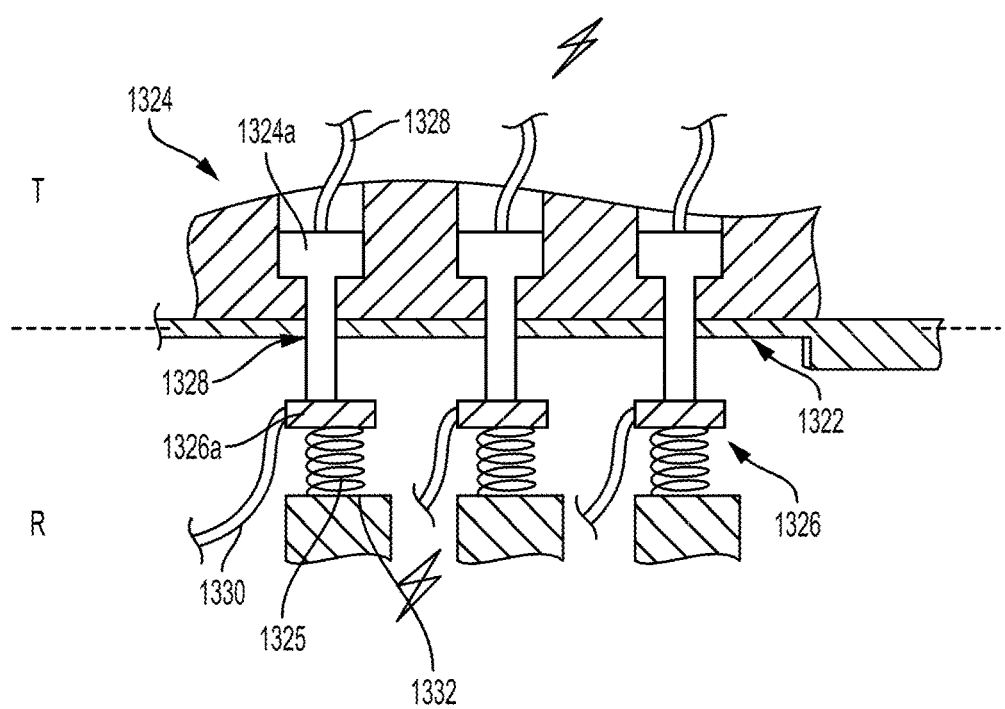
FIG. 13B illustrates another embodiment of an electrical connection formed in a sterile barrier in a surgical tool assembly.

A sterile barrier or a sterile barrier assembly can be coupled to at least one of a tool driver and a robotic arm via electrical contacts having various configurations. FIGS. 13A and 13B illustrate different types of electrical contacts that penetrate through a sterile barrier defining a sterile-side and a non-sterile side. As shown in FIG. 13A, a sterile barrier 1312 of a surgical tool assembly provides a sterile electrical interface between a side T of a tool driver and a side R of a robotic arm. Similar to the example in FIG. 12, the sterile barrier 1312 allows electrical pin contacts 1314 formed on the tool driver side to pass through the sterile barrier 1312 so as to mate with complementary electrical contacts 1316 formed on the robotic arm (not shown). For example, each pin, one of which is labeled as 1314a, passes through an opening 1318 in the sterile barrier 1312 and mates with a complementary contact 1316a. The sterile barrier 1312 is configured as a window seal such that when the electrical pin contacts 1314 mate with the electrical contacts 1316, e.g., when the tool driver coupled to a surgical tool or tool attachment of any suitable type mates with the robotic arm such that the surgical tool assembly can be utilized in a surgical procedure. In this example, the electrical pin contacts 1314 metal-doped contacts, for example, metal-doped plastic contacts or metal-doped contacts of another type. It should be appreciated that the electrical pin contacts 1314 are shown to have three pins configured to mate with respective metal-doped contacts 1316 by way of example only, as any number of pins can be formed. The connection between the electrical pin contacts 1314 and the electrical contacts 1316 allows electrical wires 1310 on the tool driver side to be connected to electrical wires 1320 on the robotic arm side.

FIG. 13B illustrates another example of electrical contacts that penetrate through a sterile barrier 1322. Electrical pin contacts 1324 formed on a tool driver side T pass through the sterile barrier 1312 so as to mate with complementary electrical contacts 1326 formed on a robotic arm side R. In this example, as shown in FIG. 13B, the electrical contacts 1326 are formed such that each pin of the electrical pin contacts 1324, one of which is labeled as 1324a, penetrates through an opening 1328 formed in the sterile barrier 1312 and mates with a corresponding contact plate 1326a coupled to an electrical wire 1330. The pin 1324a is coupled to an electrical wire 1328. The contact plate 1326a is spring biased towards the tool driver side T by a spring 1325 formed on a surface 1332. Thus, electrical connection between the tool driver and the robotic arm is established when each pin 1324a on the driver side passes through the sterile barrier 1322 and pushed against the contact plate 1326a. It should be appreciated that the electrical pin contacts 1324 are shown to have three pins configured to mate with respective spring-biased contact plates by way of example only, as any number of pins can be formed.

Regardless of the specific configuration of electrical contacts used to reversibly and replaceably connect the tool driver and the robotic arm coupled via a sterile barrier, the electrical connection is established such that the sterile environment provided by the sterile barrier is maintained.

Figure 14:
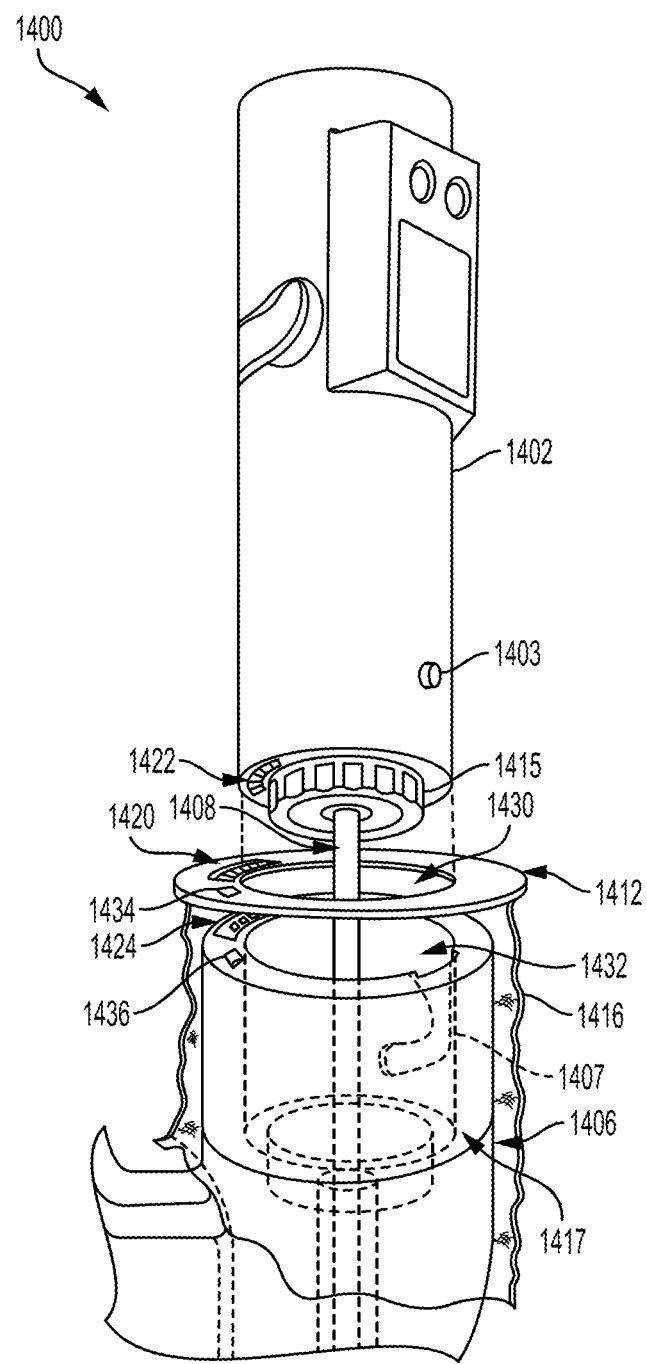
FIG. 14 illustrates an embodiment of a sterile barrier assembly.

FIG. 14 illustrates an example of a portion of a surgical tool assembly 1400 having a sterile barrier 1412 that has at least one electrical contact configured to operably mate with at least one electrical contact on a puck or tool housing 1402 and at least one electrical contact on a robotic arm 1406. In this example, the sterile barrier 1412 is a disk-shaped member having an opening 1430 configured to receive therethrough the tool housing 1402. As shown in FIG. 14, the sterile barrier 1412 has electrical contacts 1420 configured to mate with electrical contacts 1422 formed on the puck 1402 and with electrical contacts 1424 formed on a rim of the robotic arm 1406. The sterile barrier 1412 has a sterile flexible fabric 1416 extending therefrom that enshrouds the robotic arm 1406 to create a sterile field for the non-sterile arm 1406.

In the example of FIG. 14, the tool housing 1402 as shown with a surgical tool inserted therein such that a coupling ring 1415 of the tool is disposed at a distal end (the end closest to the robotic arm 1406) of the housing 1402 and a tool's shaft 1408 extends distally from the housing 1402. As shown in FIG. 14, the shaft 1408 (which can have an end effector coupled to a distal end thereof) extends through the opening 1430 in the sterile barrier 1412 and through an opening 1432 in the robotic arm 1406.

The tool housing 1402 can have various components enclosed therein, including a tool driver and other components. In this example, the tool housing 1402 is configured to reversibly mate with the robotic arm 1406 via a bayonet attachment mechanism including a bayonet attachment member and a guide member. Thus, as shown in FIG. 14, the tool housing 1402 has a bayonet attachment member 1403 on its outer wall that is configured to engage a guide member 1407 formed within the opening 1432 in the robotic arm. The guide member 1407 is configured such that it can receive the bayonet attachment member 1403 in a manner that, upon rotation of the housing 1402 with respect to the robotic arm 1406, the member 1403 is locked within the guide member 1407. To unlock the bayonet attachment mechanism, the housing 1402 is rotated in the opposite direction with respect to the robotic arm 1406. The bayonet attachment mechanism can have a number of different configurations, and the bayonet attachment member 1403 in the form of a push button is shown in FIG. 14 by way of example only.

In this example, as shown in FIG. 14, the sterile barrier 1412 defines sterile and non-sterile sides when it is disposed between a portion of the housing 1402 and the robotic arm 1406. In FIG. 14, the surgical tool assembly 1400 is shown with the robotic arm 1406 not attached to the tool housing 1402. When the housing 1402 and the robotic arm 1406 are mated such that a distal portion of the housing 1402 is received within the robotic arm 1406 (an area 1417 where that portion will be seated as shown in the partially-transparent view of the arm 1406), the sterile barrier 1412 is positioned around the housing 1402 and proximally of the bayonet attachment member 1403. In such mating position, the electrical contacts 1420 formed on the sterile barrier 1412 operably mate with the electrical contacts 1422 formed on the housing 1402 on one (sterile) side, and they also operably mate with the electrical contacts 1424 formed on the robotic arm 1406 on another (non-sterile) side. The sterile barrier 1412 can have additional features configured to mechanically couple it to the housing and/or the robotic arm. For example, as shown in FIG. 14, the sterile barrier 1412 can have a recess or opening 1434 configured to mate with a complementary tab 1436 formed on the rim of the robotic arm 1406. It should be appreciated, however, that any other features can be formed additionally or alternatively. As another option, the sterile barrier may not have any mechanical coupling mechanisms.

As discussed above, a sterile barrier in accordance with the described techniques can have various types of electrical contacts formed thereon that are configured to operably mate with at least one of a tool driver and a robotic arm. In some implementations, regardless of their specific configurations, the electrical contacts formed on the sterile barrier and on one or both of the tool driver and the arm are associated with cleaning features that allow cleaning the electrical contacts as they engage with each other. The sterile barrier can be mated with the tool driver and/or the arm via a rotary motion (e.g., a rotational motion and/or circular motion) of the components with respect to one another. The cleaning features engage with the electrical contacts during such rotary motion, and the contacts are thus cleared of debris, dirt, and any impurities. This allows maintaining the sterile barrier in a proper condition such that the sterile field created by the barrier is not compromised. Also, the cleaning reduces the possibility of electrical contacts deteriorating and malfunctioning.

Figure 15A:
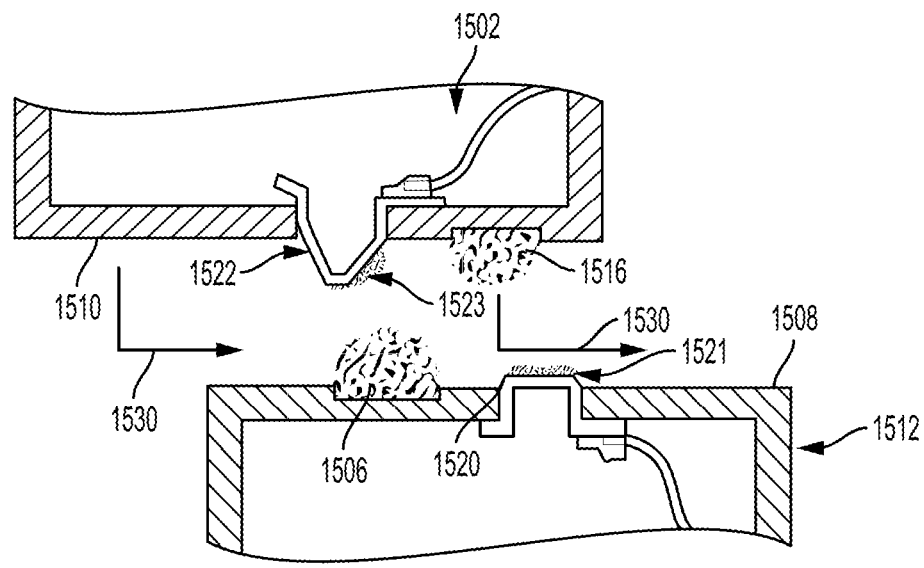
FIGS. 15A-15C illustrate an example of a configuration of an electrical connection interface between a device and a sterile barrier in a robotic surgical system, where the interface has electrical contact cleaning features associated therewith.
Figure 15B:
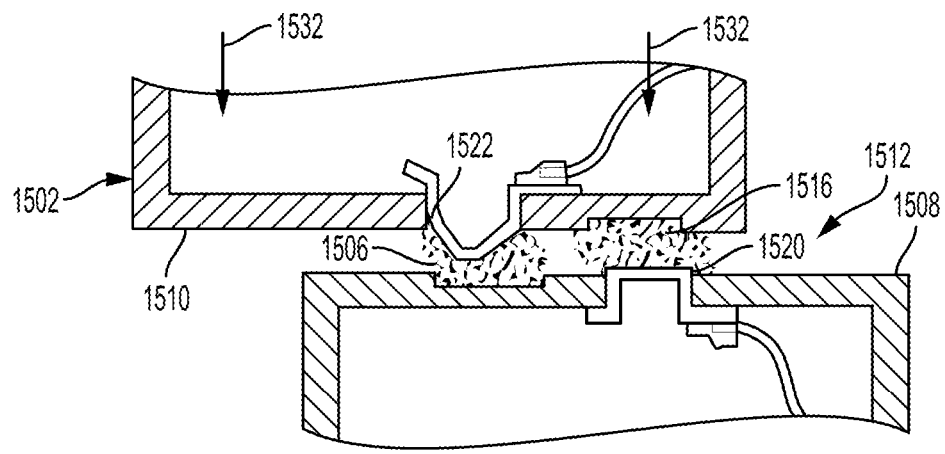
Figure 15C:
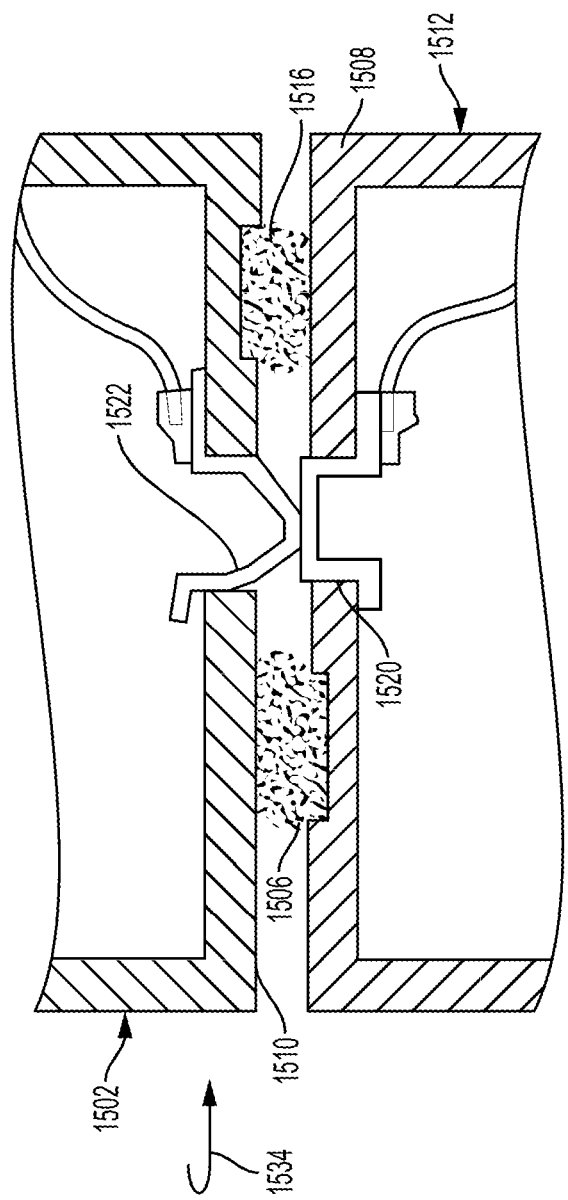

FIGS. 15A-15C illustrate schematically an example of electrical contacts that can be cleaned upon engagement. FIG. 15A shows a sterile barrier 1512 having at least one electrical contact 1520 on a surface 1508 thereof facing a component to which the sterile barriers is configured to couple. A device (e.g., a tool driver, a robotic arm, a tool housing, or other component) 1502 includes at least one electrical contact 1522 on a surface 1510 facing the surface 1508 of the sterile barrier 1512. The at least one electrical contact 1522 can be complementary to the at least one electrical contact 1520 such that the electrical contacts 1520, 1522 are configured to operably mate to provide electrical connection between the device 1502 and the sterile barrier 1512.

As shown in FIG. 15A, the surfaces 1508, 1510 have cleaning pads 1506, 1516 formed thereon such that the cleaning pad 1506 faces the at least one electrical contact 1522 on the surface 1510 of the device 1502 and the cleaning pad 1516 faces the at least one electrical contact 1520 on the surface 1508 of the sterile barrier 1512. The cleaning pads 1506, 1516 can have any suitable configuration and they can be formed in any suitable materials. In this example, they can be formed from a soft and dirt-retaining material that can be effectively used to remove debris from the electrical contacts 1520, 1522, where the debris are shown with references 1521, 1523.

The cleaning pads 1506, 1516 are configured to clean the electrical contacts 1520, 1522 upon engagement of the device 1502 and the sterile barrier 1512. FIG. 15A illustrates by arrows 1530 a direction in which the device 1502 is moved with respect to sterile barrier 1512 for these components to mate such that the electrical contacts 1520, 1522 are operably mated.

FIG. 15B illustrates a subsequent position of the device 1502 with respect to the sterile barrier 1512 when the device 1502 is moved towards the sterile barrier 1512, as shown by arrows 1532. As shown in FIG. 15B, when the device 1502 is moved in this way, the cleaning pad 1506 aligns with and touches the electrical contact 1522 and the cleaning pad 1516 aligns with and touches the electrical contact 1520. The cleaning pads 1506, 1516 thus are in contact with the debris disposed on the electrical contacts. As the device 1502 is then rotated with respect to the sterile barrier 1512 (or vice versa), as shown by arrow 1534 in FIG. 15C, the cleaning pad 1506 is swiped against the electrical contact 1522 and the cleaning pad 1516 is swiped against the electrical contact 1520. In this way, as the device and the sterile barrier are brought into operable engagement, the electrical contacts 1520, 1522 are cleaned of debris and other impurities. The further rotational movement causes the electrical contacts 1520, 1522 to be positioned in alignment with respect to one another such that they are operably mated as shown in FIG. 15C. The cleaning pads 1506, 1516 can have configuration and properties such that they do not interfere with establishing the contact and electrical connection between the electrical contacts 1520, 1522, as schematically shown in FIG. 15C. For example, the pads 1506, 1516 can be formed from a material that allows them to contract when they are disposed between the surfaces 1508, 1510, which can apply some pressure to the pads, as shown in FIG. 15C. The pads can expand when the device 1502 and the sterile barrier 1512 are disconnected from one another.

It should be appreciated that the cleaning pads are shown in FIGS. 15A-15C by way of example only, as any other types of features can be used for cleaning of the electrical contacts. Also, the electrical contacts 1520, 1522 can have many various configurations, including any of the configurations described herein. It should in addition be appreciated that, while one of the electrical contacts 1520, 1522 is shown in FIGS. 15A-15C, any suitable number of electrical contacts can be formed on the sterile barrier and the device (e.g., a tool driver, a robotic arm, or any other device engaging with the sterile barrier).

As will be appreciated by those skilled in the art, specification of the presence of stated features, steps, operations, elements, and/or components does not preclude the presence or addition of one or more other features, steps, operations, elements, components, and/or groups described herein. In addition, components described as coupled may be directly coupled, or they may be indirectly coupled via one or more intermediate components.

There are several general aspects that apply to the various descriptions below. For example, at least one surgical end effector is shown and described in various figures. An end effector is the part of a surgical instrument or assembly that performs a specific surgical function, e.g., forceps/graspers, needle drivers, scissors, electrocautery hooks, staplers, clip appliers/removers, suction tools, irrigation tools, etc. Any end effector can be utilized with the surgical systems described herein. Further, in exemplary embodiments, an end effector can be configured to be manipulated by a user input tool. The input tool can be any tool that allows successful manipulation of the end effector, whether it be a tool similar in shape and style to the end effector, such as an input tool of scissors similar to end effector scissors, or a tool that is different in shape and style to the end effector, such as an input tool of a glove dissimilar to end effector graspers, and such as an input tool of a joystick dissimilar to end effector graspers. In some embodiments, the input tool can be a larger scaled version of the end effector to facilitate ease of use. Such a larger scale input tool can have finger loops or grips of a size suitable for a user to hold. However, the end effector and the input tool can have any relative size.

A slave tool, e.g., a surgical instrument, of the surgical system can be positioned inside a patient's body cavity through an access point in a tissue surface for minimally invasive surgical procedures. Typically, cannulas such as trocars are used to provide a pathway through a tissue surface and/or to prevent a surgical instrument or guide tube from rubbing on patient tissue. Cannulas can be used for both incisions and natural orifices. Some surgical procedures require insufflation, and the cannula can include one or more seals to prevent excess insufflation gas leakage past the instrument or guide tube. In some embodiments, the cannula can have a housing coupled thereto with two or more sealed ports for receiving various types of instruments besides the slave assembly. As will be appreciated by a person skilled in the art, any of the surgical system components disclosed herein can have a functional seal disposed thereon, therein, and/or therearound to prevent and/or reduce insufflation leakage while any portion of the surgical system is disposed through a surgical access port, such as a cannula. The surgical systems can also be used in open surgical procedures. As used herein, a surgical access point is a point at which the slave tool enters a body cavity through a tissue surface, whether through a cannula in a minimally invasive procedure or through an incision in an open procedure.

Reuse

The devices disclosed herein can also be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, components of the invention described herein will be processed before use. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high energy electrons. The radiation kills bacteria on the instrument and in the container. The sterilized instrument can then be stored in the sterile container. The sealed container keeps the instrument sterile until it is opened in the medical facility.

Typically, the device is sterilized. This can be done by any number of ways known to those skilled in the art including beta or gamma radiation, ethylene oxide, steam, and a liquid bath (e.g., cold soak). An exemplary embodiment of sterilizing a device including internal circuitry is described in more detail in U.S. Pat. No. 8,114,345 entitled "System And Method Of Sterilizing An Implantable Medical Device." It is preferred that device, if implanted, is hermetically sealed. This can be done by any number of ways known to those skilled in the art.

One skilled in the art will appreciate further features and advantages of the disclosed systems and methods based on the above-described embodiments. Accordingly, the present disclosure is not to be limited by what has been particularly shown and described, except as indicated by the appended claims. All publications and references cited herein are expressly incorporated herein by reference in their entirety.

What is claimed is:

1. A sterile barrier for use with a robotic surgical system, comprising:
a housing configured to mate with a tool driver mated to a robotic arm and to removably receive a surgical tool, the housing having a sterile flexible fabric extending therefrom such that the housing and the flexible fabric are formed in more than one plane and define a sterile side on which the surgical tool is disposed and a non-sterile side on which the tool driver and the robotic arm are disposed, the housing further having a substantially rigid, generally cylindrical elongate member and a substantially c-shaped cross section, and the housing further having
an opening for receiving the surgical tool, and
at least one electrical contact configured to operably mate with at least one electrical contact on at least one of the tool driver and the robotic arm.

2. The surgical system of claim 1, wherein the housing has a first side that is configured to be received within and mate with an opening in the tool driver and a second side, opposite the first side.

3. The surgical system of claim 1, wherein the housing opening is an elongate slit.

4. The surgical system of claim 1, wherein the housing is formed of an annular rim, a first section, and a second section, the annular rim is configured to attach the sterile flexible fabric therefrom such that an exterior portion of the housing defines the sterile side and an interior portion of the housing defines the non-sterile side, the first section having at least one electrical contact to operably mate with at least one electrical contact on at least one of the tool driver and the robotic arm, and the second section having a nominal diameter less than the first section to receive an interchangeable shaft coupled to the surgical tool.

5. The surgical system of claim 1, wherein the sterile flexible fabric comprises a polymeric of an elastic membrane.

6. The surgical system of claim 1, wherein the electrical contacts on a portion of the surgical tool are formed on a puck portion of the surgical tool.

7. The sterile barrier of claim 1, wherein the housing opening is formed on a first side of the housing.

8. The sterile barrier of claim 1, wherein the housing further includes a first tool region having a first width adjacent to a second tool region having a second width.

9. A sterile barrier for use with a robotic surgical system, comprising:
a housing having a substantially c-shaped cross-section and configured to mate with a tool driver mated to a robotic arm and to removably receive a surgical tool, the housing including:
an annular rim disposed on a first end of the housing;
a sterile flexible fabric coupled to the housing such that the housing and the sterile flexible fabric are formed in more than one plane; and
a first section adjacent to the annular rim and having a substantially c-shaped cross section and at least one electrical contact configured to operably mate with at least one electrical contact on at least one of the tool driver and the robotic arm.

10. The sterile barrier of claim 9, wherein the first section further includes at least one slot configured to mate with a portion of a surgical tool.

11. The sterile barrier of claim 9, wherein the housing further includes a second section proximate to the first section, the second section configured to receive a shaft of the surgical tool.

12. The sterile barrier of claim 9, wherein the housing further includes an opening formed on a first side of the housing.

13. The sterile barrier of claim 9, wherein the housing further includes a first tool region having a first width adjacent to a second tool region having a second width.

\* \* \* \* \*